(12) United States Patent
Narayan et al.

(10) Patent No.: US 9,439,573 B2
(45) Date of Patent: *Sep. 13, 2016

(54) METHOD FOR ANALYSIS OF COMPLEX RHYTHM DISORDERS

(71) Applicant: The Regents of the University of California, Oakland, CA (US)

(72) Inventors: Sanjiv Narayan, La Jolla, CA (US); Wouter-Jan Rappel, San Diego, CA (US)

(73) Assignees: The Regents of the University of California, Oakland, CA (US); The United States of America as Represented by the Department of Veterans Affairs, Washington, DC (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/473,456

(22) Filed: Aug. 29, 2014

(65) Prior Publication Data

US 2014/0371616 A1    Dec. 18, 2014

Related U.S. Application Data

(63) Continuation of application No. 14/062,848, filed on Oct. 24, 2013, now Pat. No. 8,838,223, which is a continuation of application No. 13/964,604, filed on Aug. 12, 2013, which is a continuation of application No. 12/576,809, filed on Oct. 9, 2009, now Pat. No. 8,521,266.

(60) Provisional application No. 61/195,866, filed on Oct. 9, 2008.

(51) Int. Cl.
*A61B 5/04* (2006.01)
*A61B 5/024* (2006.01)
(Continued)

(52) U.S. Cl.
CPC ............. *A61B 5/02405* (2013.01); *A61B 5/02* (2013.01); *A61B 5/0245* (2013.01); *A61B 5/04* (2013.01); *A61B 5/0402* (2013.01); *A61B 5/044* (2013.01); *A61B 5/046* (2013.01);
(Continued)

(58) Field of Classification Search
CPC ...... A61B 5/02; A61B 5/04; A61B 5/04012; A61B 5/0402; A61B 5/0452; A61B 5/046
See application file for complete search history.

(56) References Cited

U.S. PATENT DOCUMENTS

| 5,121,750 A | 6/1992 | Katims |
| 5,172,699 A | 12/1992 | Svenson et al. |

(Continued)

FOREIGN PATENT DOCUMENTS

WO    2008035070 A3    3/2008

OTHER PUBLICATIONS

PCT/US2014/029616 International Search Report and Written Opinion, Sep. 18, 2014; 9 pages.
(Continued)

*Primary Examiner* — Eric D. Bertram
(74) *Attorney, Agent, or Firm* — Eleanor Musick; Musick Davison LLP

(57) ABSTRACT

A method of analyzing a complex rhythm disorder in a human heart includes accessing signals from a plurality of sensors disposed spatially in relation to the heart, where the signals are associated with activations of the heart, and identifying a region of the heart having an activation trail that is rotational or radially emanating, where the activation trail is indicative of the complex rhythm disorder and is based on activation times associated with the activations of the heart.

81 Claims, 15 Drawing Sheets
(3 of 15 Drawing Sheet(s) Filed in Color)

(51) Int. Cl.

| | | |
|---|---|---|
| *A61B 5/02* | (2006.01) | |
| *A61B 5/0402* | (2006.01) | |
| *A61B 5/046* | (2006.01) | |
| *A61B 5/0464* | (2006.01) | |
| *A61B 18/14* | (2006.01) | |
| *A61B 5/0452* | (2006.01) | |
| *A61B 18/12* | (2006.01) | |
| *A61B 5/0245* | (2006.01) | |
| *A61B 5/044* | (2006.01) | |
| *A61B 5/00* | (2006.01) | |
| *A61B 18/00* | (2006.01) | |

(52) U.S. Cl.
CPC ...... *A61B 5/04011* (2013.01); *A61B 5/04012* (2013.01); *A61B 5/0452* (2013.01); *A61B 5/0464* (2013.01); *A61B 5/4836* (2013.01); *A61B 5/6859* (2013.01); *A61B 18/1206* (2013.01); *A61B 18/1492* (2013.01); *A61B 5/7203* (2013.01); *A61B 5/726* (2013.01); *A61B 2018/00214* (2013.01); *A61B 2018/00357* (2013.01); *A61B 2018/00375* (2013.01); *A61B 2018/00839* (2013.01); *A61B 2018/1435* (2013.01)

(56) References Cited

U.S. PATENT DOCUMENTS

| | | | |
|---|---|---|---|
| 5,427,112 | A | 6/1995 | Noren et al. |
| 5,433,198 | A | 7/1995 | Desai |
| 5,450,846 | A | 9/1995 | Goldreyer |
| 5,480,422 | A | 1/1996 | Ben-Haim |
| 5,487,391 | A | 1/1996 | Panescu |
| 5,582,173 | A | 12/1996 | Li |
| 5,657,755 | A | 8/1997 | Desai |
| 5,662,108 | A | 9/1997 | Budd et al. |
| 5,687,737 | A | 11/1997 | Branham et al. |
| 5,718,241 | A | 2/1998 | Ben-Haim et al. |
| 5,795,303 | A | 8/1998 | Swanson et al. |
| 5,817,134 | A | 10/1998 | Greenhut et al. |
| 5,840,025 | A | 11/1998 | Ben-Haim |
| 5,848,972 | A | 12/1998 | Triedman et al. |
| 5,868,680 | A | 2/1999 | Steiner et al. |
| 5,954,665 | A | 9/1999 | Ben-Haim |
| 6,052,618 | A | 4/2000 | Dahlke et al. |
| 6,066,094 | A | 5/2000 | Ben-Haim |
| 6,115,628 | A | 9/2000 | Stadler et al. |
| 6,188,924 | B1 | 2/2001 | Swanson et al. |
| 6,236,883 | B1* | 5/2001 | Ciaccio ............ A61B 5/04525 600/515 |
| 6,256,540 | B1 | 7/2001 | Panescu et al. |
| 6,301,496 | B1 | 10/2001 | Reisfeld |
| 6,360,121 | B1 | 3/2002 | Shoda |
| 6,522,905 | B2 | 2/2003 | Desai |
| 6,584,345 | B2 | 6/2003 | Govari |
| 6,847,839 | B2 | 1/2005 | Ciaccio et al. |
| 6,856,830 | B2 | 2/2005 | He |
| 6,892,091 | B1 | 5/2005 | Ben-Haim et al. |
| 6,920,350 | B2 | 7/2005 | Xue et al. |
| 6,941,166 | B2 | 9/2005 | MacAdam et al. |
| 6,959,212 | B2 | 10/2005 | Hsu et al. |
| 6,975,900 | B2 | 12/2005 | Rudy et al. |
| 6,978,168 | B2 | 12/2005 | Beatty et al. |
| 7,016,719 | B2 | 3/2006 | Rudy et al. |
| 7,043,292 | B2 | 5/2006 | Tarjan et al. |
| 7,117,030 | B2 | 10/2006 | Berenfeld et al. |
| 7,123,954 | B2 | 10/2006 | Narayan et al. |
| 7,206,630 | B1 | 4/2007 | Tarler |
| 7,245,962 | B2 | 7/2007 | Ciaccio et al. |
| 7,263,397 | B2 | 8/2007 | Hauck et al. |
| 7,283,865 | B2 | 10/2007 | Noren |
| 7,289,843 | B2 | 10/2007 | Beatty et al. |
| 7,328,063 | B2 | 2/2008 | Zhang et al. |
| 7,505,810 | B2 | 3/2009 | Harlev et al. |
| 7,515,954 | B2 | 4/2009 | Harlev et al. |
| 7,751,882 | B1 | 7/2010 | Helland |
| 7,761,142 | B2 | 7/2010 | Ghanem et al. |
| 7,761,150 | B2 | 7/2010 | Ghanem et al. |
| 7,907,994 | B2 | 3/2011 | Stolarski et al. |
| 7,930,018 | B2 | 4/2011 | Harlev et al. |
| 7,930,020 | B2 | 4/2011 | Zhang et al. |
| 8,165,666 | B1 | 4/2012 | Briggs et al. |
| 8,165,671 | B2 | 4/2012 | Freeman et al. |
| 8,175,702 | B2 | 5/2012 | Efimov et al. |
| 8,521,266 | B2* | 8/2013 | Narayan ............ A61B 5/046 600/515 |
| 8,594,777 | B2 | 11/2013 | Briggs et al. |
| 8,639,325 | B2 | 1/2014 | Efimov et al. |
| 8,676,303 | B2 | 3/2014 | Narayan |
| 8,700,140 | B2 | 4/2014 | Narayan et al. |
| 8,838,222 | B2* | 9/2014 | Narayan ............ A61B 5/046 600/515 |
| 8,838,223 | B2* | 9/2014 | Narayan ............ A61B 5/046 600/515 |
| 2002/0010392 | A1 | 1/2002 | Desai |
| 2003/0236466 | A1 | 12/2003 | Tarjan |
| 2004/0073262 | A1 | 4/2004 | Lovett |
| 2004/0243012 | A1* | 12/2004 | Ciaccio ............ A61B 5/04011 600/509 |
| 2005/0148892 | A1 | 7/2005 | Desai |
| 2005/0203502 | A1 | 9/2005 | Boveja et al. |
| 2006/0084970 | A1 | 4/2006 | Beatty et al. |
| 2006/0161206 | A1* | 7/2006 | Efimov ............ A61B 5/0402 607/5 |
| 2007/0055167 | A1 | 3/2007 | Bullinga |
| 2007/0208260 | A1 | 9/2007 | Afonso |
| 2007/0299351 | A1 | 12/2007 | Harlev et al. |
| 2008/0097539 | A1 | 4/2008 | Belalcazar et al. |
| 2008/0109041 | A1 | 5/2008 | de Voir |
| 2008/0114258 | A1 | 5/2008 | Zhang et al. |
| 2009/0069704 | A1 | 3/2009 | MacAdam et al. |
| 2009/0099468 | A1 | 4/2009 | Thiagalingam et al. |
| 2009/0112106 | A1 | 4/2009 | Zhang |
| 2009/0112110 | A1 | 4/2009 | Zhang |
| 2009/0112199 | A1 | 4/2009 | Zhang et al. |
| 2009/0177071 | A1 | 7/2009 | Harlev et al. |
| 2009/0177072 | A1 | 7/2009 | Harlev et al. |
| 2009/0299424 | A1 | 12/2009 | Narayan |
| 2010/0094274 | A1 | 4/2010 | Narayan |
| 2010/0204592 | A1 | 8/2010 | Hatib et al. |
| 2010/0217143 | A1 | 8/2010 | Whittington et al. |
| 2010/0239627 | A1 | 9/2010 | Whitekettle et al. |
| 2010/0298729 | A1 | 11/2010 | Zhang et al. |
| 2010/0305456 | A1 | 12/2010 | Brainard, II |
| 2011/0087121 | A1 | 4/2011 | Zhang et al. |
| 2011/0112425 | A1 | 5/2011 | Muhlsteff et al. |
| 2011/0130801 | A1 | 6/2011 | Maskara et al. |
| 2011/0196249 | A1 | 8/2011 | Staeuber et al. |
| 2011/0251505 | A1 | 10/2011 | Narayan |
| 2011/0257547 | A1 | 10/2011 | Zhang et al. |
| 2011/0282227 | A1 | 11/2011 | Zhang |
| 2012/0232417 | A1 | 9/2012 | Zhang et al. |
| 2012/0283579 | A1 | 11/2012 | Briggs et al. |
| 2013/0006131 | A1 | 1/2013 | Narayan et al. |
| 2013/0150740 | A1 | 6/2013 | Narayan et al. |
| 2013/0150742 | A1 | 6/2013 | Briggs et al. |
| 2013/0226016 | A1 | 8/2013 | Narayan et al. |
| 2013/0331718 | A1 | 12/2013 | Narayan et al. |
| 2014/0066787 | A1 | 3/2014 | Narayan et al. |
| 2014/0073981 | A1 | 3/2014 | Narayan et al. |
| 2014/0114204 | A1 | 4/2014 | Narayan et al. |
| 2014/0228696 | A1 | 8/2014 | Narayan et al. |
| 2014/0276152 | A1 | 9/2014 | Narayan et al. |

OTHER PUBLICATIONS

Houben, R.P.M., et al, "Automatic mapping of human atrial fibrillation by template matching", Heart Rhythm, vol. 3, No. 10, Oct. 1, 2006, pp. 1221-1228.

Nademanee, Koonlawee, et al., "A new approach for catheter ablation of atrial fibrillation: mapping of the electrophysiologic substrate", J. Amer.Coll.Cardiol., vol. 43, No. 11, Jun. 2, 2004, pp. 2044-2053.

(56) References Cited

OTHER PUBLICATIONS

Narayan, S.M., et al., "Dynamics factors preceding the initiation of atrial fibrillation in humans", Heart Rhythm, vol. 5, No. 6, Jun. 1, 2008, pp. S22-S25.

Ciaccio, Edward J. et al., "Development of Gradient Descent Adaptive Algorithms to Remove Common Mode Artifact for Improvement of Cardiovascular Signal Quality", Annals of Biomedical Engineering, vol. 35, No. 7, Jul. 2007, pp. 1146-1155.

Sornborger, Andrew, et al., "Extraction of Periodic Multivariate Signals: Mapping of Voltage-Dependent Dye Fluorescence in the Mouse Heart", IEEE Transactions on Medical Imaging, vol. 22, No. 12, Dec. 2003, pp. 1537-1549.

Sun, Yan, et al., "Characteristic wave detection in ECG signal using morphological transform", BMC Cardiovascular Disorders, vol. 5, No. 28, 2005.

Tai, Dean C.S., et al., "Correction of motion artifact in transmembrane voltage-sensitive fluorescent dye emission in hearts", Am. J. Physiol. Heart Circ. Physiol., vol. 287, 2004, pp. H985-H993.

Lin, Y-J, et al., "Electrophysiological Characteristics and Catheter Ablation in Patients With Paroxysmal Right Atrial Fibrillation", Circulation, Sep. 20, 2005; 112(12): 1692-1700, EPub Sep. 12, 2005.

Houben, R.P.M., et al., "Processing of Intracardiac Electrograms in Atrial Fibrillation", IEEE Engineering in Medicine and Biology Magazine, Nov./Dec. 2006, pp. 40-51.

Saksena, S., et al., "Regional Endocardial Mapping of Spontaneous and Induced Atrial Fibrillation in Patients With Heart Disease and Refractory Atrial Fibrillation", Am J Cardiol, 1999; 84:880-889.

PCT/US2011/031468: International Preliminary Report on Patentability, Oct. 9, 2012, 8 pages.

PCT/US2009/060178: International Preliminary Report on Patentability, Apr. 12, 2011, 10 pages.

PCT/US2011/031470: International Preliminary Report on Patentability, Oct. 9, 2012, 7 pages.

PCT/US2012/029935: International Search Report and Written Opinion, Nov. 8, 2012, 9 pages.

PCT/US2012/036157: International Preliminary Report on Patentability, Nov. 5, 2013, 8 pages.

PCT/US2012/068640: International Preliminary Report on Patentability, Jun. 10, 2014, 5 pages.

PCT/US2012/068639: International Preliminary Report on Patentability, Jun. 10, 2014, 6 pages.

EP09819953: Supplementary European Search Report and European Search Opinion, Feb. 7, 2012, 5 pages.

EP12711553: Supplementary European Search Report and European Search Opinion, Sep. 11, 2013, 7 pages.

Umapathy, K, et al. "Spatiotemporal Frequency Analysis of Ventricular Fibrillation in Explanted Human Hearts," IEEE Transactions in Biomedical Engineering, IEEE Service Center, Piscataway, NJ USA, vol. 56, No. 2, Feb. 1, 2009, pp. 328-335.

Kalifa, J, et al. "Mechanisms of wave fractionation at boundaries of high-frequency excitation in the posterior left atrium of the isolated sheep heart during atrial fibrillation," Circulation, vol. 113, No. 5, Feb. 7, 2006, pp. 626-633.

Yenn-Jiang L, et al. "Electrophysiological Mechanisms and Catheter Ablation of Complex Atrial Arrhythmias from Crista Terminalis: Insight from Three-Dimentional Noncontact Mapping," Pacing and Clinical Electrophysiology, vol. 27, No. 9, Sep. 1, 2004, pp. 1231-1239.

Supplementary European Search Report & European Search Opinion issued in EP 12779506.0, mailed Nov. 18, 2011, 8 pages.

\* cited by examiner

FIG. 12A  FIG. 12B

METHOD FOR ANALYSIS OF COMPLEX RHYTHM DISORDERS

RELATED APPLICATIONS

This application is a continuation of U.S. application Ser. No. 14/062,848, filed Oct. 24, 2013, issued Sep. 16, 2014, as U.S. Pat. No. 8,838,223, which is a continuation of U.S. application Ser. No. 13/964,604, filed Aug. 12, 2013, which is a continuation of U.S. application Ser. No. 12/576,809, filed Oct. 9, 2009, issued Aug. 27, 2013, as U.S. Pat. No. 8,521,266, which claims the benefit of the priority of provisional application 61/195,866, filed Oct. 9, 2008, each of which is herein incorporated by reference in its entirety.

GOVERNMENT RIGHTS

This invention was made with government support under Grants HL070529 and HL083359 awarded by the National Institutes of Health. The government has certain rights in the invention.

FIELD OF THE INVENTION

This invention relates generally to the field of medicine and more specifically to a method, system and machine for diagnosing, finding the source for and treating irregularities and other disorders of biological rhythms. In particular, the present invention can be applied to minimally invasive techniques or surgical techniques to detect, diagnose and treat the disorder. One embodiment directs this invention to disorders of heart rhythm, another to electrical disorders of the brain and nervous system and others to electrical or contractile disorders of the smooth muscle of the gastrointestinal and genitourinary systems.

BACKGROUND OF RELATED ART

Heart rhythm disorders are very common in the United States, and are significant causes of morbidity, lost days from work, and death. Heart rhythm disorders exist in many forms, of which the most complex and difficult to treat are atrial fibrillation (AF), ventricular tachycardia (VT) and ventricular fibrillation (VF). Other rhythms are more simple to treat, but may also be clinically significant including atrial tachycardia (AT), supraventricular tachycardia (SVT), atrial flutter (AFL), premature atrial complexes/beats (SVE) and premature ventricular complexes/beats (PVC). Under certain conditions, rapid activation of the normal sinus node can cause the heart rhythm disorder of inappropriate sinus tachycardia or sinus node reentry.

Treatment of heart rhythm disorders, particularly the complex ones of AF, VF and VT, can be very difficult. Pharmacologic therapy is particularly suboptimal for AF (Singh, Singh et al. 2005) and VT or VF (Bardy, Lee et al. 2005) and, as a result, there is considerable interest in non-pharmacologic therapy. Ablation is a promising and increasingly used therapy to eliminate heart rhythm disorders by maneuvering a sensor/probe to the heart through the blood vessels, or directly at surgery, then delivering energy to the cause(s) for the heart rhythm disorder to terminate it. Ablation was initially used for "simple" disorders such as SVT. AFL. PVC, PAC, but is increasingly used for AF (Cappato, Calkins et al. 2005). VT (Reddy, Reynolds et al. 2007) and, to a lesser extent, VF (Knecht, Sacher et al. 2009).

However, ablation is often difficult because tools to identify and locate the cause of the heart rhythm disorder are poor, hindering attempts to deliver energy to the correct region to terminate and eliminate the disorder. In persistent AF, a highly prevalent form of AF, ablation has a one procedure success rate of only 50-60% (Cheema, Vasamreddy et al. 2006; Calkins, Brugada et al. 2007) despite lengthy 4-5 hour procedures and a 5-10% rate of serious complications (Ellis, Culler et al. 2009) including death (Cappato, Calkins et al. 2009). Even for 'simple' disorders such as atrial tachycardia, tools do not exist to make the diagnosis and suggest a likely successful ablation location.

Even the most sophisticated known systems display data that the practitioner has to interpret, without directly identifying and locating the cause of the disorder to enable the practitioner to detect, diagnose and treat it. This includes currently used methods, described in U.S. Pat. No. 5,662,108, U.S. Pat. No. 5,662,108, U.S. Pat. No. 6,978,168, U.S. Pat. No. 7,289,843 and others by Beatty and coworkers, U.S. Pat. No. 7,263,397 by Hauck and Schultz, U.S. Pat. No. 7,043,292 by Tarjan and coworkers, U.S. Pat. No. 6,892,091 and other patents by Ben-Haim and coworkers and U.S. Pat. No. 6,920,350 by Xue and coworkers. These methods and instruments detect, analyze and display electrical potentials, often in sophisticated 3-dimensional anatomic representations, but still fail to identify and locate the cause of heart rhythm disorders, particularly for complex disorders such as AF. This is also true for patents by Rudy and coworkers (U.S. Pat. Nos. 6,975,900 and 7,016,719, among others), which use signals from the body surface to "project" potentials on the heart.

Certain known methods for identifying and locating causes for heart rhythm disorders may work in simple rhythm disorders, but there are no known methods that have been successful with respect to identifying causes for complex disorders such as AF. VF or polymorphic VT. Activation mapping (tracing activation back to the earliest site) is useful only for simple tachycardias, works poorly for AFL (a continuous rhythm without a clear "start"), and not at all for AF with variable activation paths. Entrainment mapping uses pacing to identify sites where the stimulating electrode is at the cause of a rhythm, yet pacing cannot be applied in AF and even some "simple" rhythms such as atrial tachycardias due to automatic mechanisms. Stereotypical locations are known for the cause(s) of atrioventricular node reentry, typical AFL and patients with early (paroxysmal) AF, but not for the vast majority of patients with persistent AF (Calkins, Brugada et al. 2007), VF and other complex disorders. Thus, no methods yet exist to identify and locate the cause of complex heart rhythm disorders such as AF (Calkins, Brugada et al. 2007).

As an example of systems for "simple" rhythms with consistent activation from beat to beat is given by U.S. Pat. No. 5,172,699 by Svenson and King. This system is based upon finding diastolic intervals, which can be defined in "simple rhythms," but no complex rhythms such as atrial fibrillation (AF) or ventricular fibrillation (VF) (Calkins, Brugada et al. 2007; Waldo and Feld 2008). Moreover, this system does not identify or locate a cause, since it is examines diastolic intervals (between activations) rather than activation itself. In addition, it is focused on ventricular tachycardia rather than AF or VF, since it analyzes periods of time between QRS complexes on the ECG.

Another example is U.S. Pat. No. 6,236,883 by Ciaccio and Wit. This invention uses a concentric array of electrodes to identify and localize reentrant circuits. Accordingly, this will not find non-reentrant causes such as focal beats.

Moreover, this method of using feature and detection localization algorithms will not work for complex rhythms such as AF and VF, where activation within the heart changes from beat to beat. It identifies "slow conduction within an isthmus of the reentry circuit", which are features of "simple" arrhythmias such as ventricular tachycardia, but are not defined for AF and VF.

In a later U.S. Pat. No. 6,847,839, Ciaccio and coworkers describe an invention to identify and localize a reentry circuit in normal (sinus) rhythm. Again, this will not find causes for an arrhythmia that are not reentrant but focal, from where activation emanates radially. Second, this patent is based on the presence in sinus rhythm of an "isthmus" for reentry, which is accepted for 'simple' rhythms with consistent activation between beats such as VT (see (Reddy, Reynolds et al. 2007)). However, this is not accepted for complex rhythms with varying activation paths such as AF or VF.

U.S. Pat. No. 6,522,905 by Desai describes an invention that uses the principle of finding the earliest site of activation, and determining this to be the cause of an arrhythmia. This approach will not work for simple arrhythmias due to reentry, in which there is no "earliest" site in reentry because activation is a continuous "circle." This approach will also not work for complex arrhythmias in which activation varies from beat to beat, such as AF or VF.

However, even in simple heart rhythm disorders, it is often difficult to apply known methods to identify causes. For instance, ablation success for atrial tachycardias (a "simple" disorder) may be as low as 70%. When surgeons perform heart rhythm disorder procedures (Cox 2004; Abreu Filho, 2005) it is ideal for them to be assisted by an expert in heart rhythm disorders (cardiac electrophysiologist). Thus, ablating the cause of a heart rhythm disorder can be challenging, and even experienced practitioners may require hours to ablate certain "simple" rhythm disorders (with consistent beat-to-beat activation patterns) such as atrial tachycardia or atypical (left atrial) AFL. The situation is more difficult still for complex heart rhythm disorders such as AF and VF where activation sequences alter from beat-to-beat.

In the absence of methods to identify and locate causes for human AF, physicians have often turned to the animal literature. In animal models, localized causes for complex and irregular AF (induced by artificial means) have been identified and located in the form of localized "electrical rotors" or repetitive focal beats (Skanes, Mandapati et al. 1998; Warren, Guha et al. 2003). In animals, rotors are indicated by signals that show a high spectral dominant frequency (DF) (a fast rate) and a narrow DF (indicating regularity) (Kalifa, Tanaka et al. 2006). Such uses of spectral dominant frequencies are described in U.S. Pat. No. 7,117,030 issued to Berenfeld and coworkers.

Unfortunately, these animal data have not translated into effective human therapy. Animal models of AF and VF likely differ from human disease. For instance, animal AF is rarely spontaneous, it rarely initiates from pulmonary vein triggers (that are common in human paroxysmal AF). Both AF and VF are typically studied in young animals without the multiple co-existing pathology (Wijffels, Kirchhof et al. 1995; Gaspo, Bosch et al. 1997; Allessie, Ausma et al. 2002) seen in older humans who typically experience these conditions.

In AF patients, sites where rate is high (or, sites of high spectral dominant frequency, DF) have not been useful targets for ablation. A recent study by Sanders and coworkers showed that AF rarely terminated with ablation at sites of high DF (Sanders, Berenfeld et al. 2005a). Other studies show that sites of high DF are common in the atrium, and ablation at these sites does not acutely terminate AF (as would be expected if high DF sites were causes) (Calkins, Brugada et al. 2007). In part, this may be because the DF method that is effective in animals may be inaccurate in human AF for many reasons, as shown by many workers (Ng, Kadish et al. 2006; Narayan, Krummen et al. 2006d; Ng, Kadish et al. 2007). Nademanee and coworkers have suggested that signals of low amplitude with high-frequency components (complex fractionated atrial electrograms, CFAE) may indicate AF causes (Nademanee, McKenzie et al. 2004a). This diagnostic method has been incorporated into commercial systems by Johnson and Johnson/Biosense. However, this method has also been questioned. Oral and coworkers showed that ablation of CFAE does not terminate AF or prevent AF recurrence alone (Oral, Chugh et al. 2007) or when added to existing ablation (Oral, Chugh et al. 2009).

Several inventions in the prior art acknowledge what was felt true until now—that AF is a "cardiac arrhythmia with no detectable anatomical targets, i.e., no fixed aberrant pathways," such as U.S. Pat. No. 5,718,241 by Ben-Haim and Zachman. This patent, as a result, does not identify and locate the cause for a heart rhythm disorder. Instead, it focuses treatment on heart geometry by delivering lines of ablation to "interrupt each possible geometric shape." This patent creates maps of various parameters of the heart.

Many inventions use surrogates for the actual cause for a cardiac arrhythmia, without identifying and locating said cause. For instance, U.S. Pat. No. 5,868,680 by Steiner and Lesh uses measures of organization within the heart that are constructed by comparing the activation sequence for one activation event (beat) to the activation sequence for subsequent beats, to determine if "any spatiotemporal order change has occurred". However, that invention assumes that organization is greatest near a critical site for AF and is lower at other sites. However, this assumption may not be correct. In animal studies, indexes of organization fall with distance from an AF source then actually increase again as activation re-organizes at more distant sites (Kalifa, Tanaka et al. 2006). Moreover, U.S. Pat. No. 5,868 requires more than one beat. As a result, methods such as described in U.S. Pat. No. 5,868,680 identify many sites, most of which most are not causes of AF. This lack of identifying and locating a cause for AF may explain why methods based on organization have not yet translated into improved treatment to acutely terminate AF. Similarly, U.S. Pat. No. 6,301,496 by Reisfeld is based on the surrogate of mapping physiologic properties created from a local activation time and vector function. This is used to map conduction velocity, or another gradient function of a physiologic property, on a physical image of the heart. However, this patent does not identify or locate a cause of a heart rhythm disorder. For instance, multiple activation paths in AF mean that the conduction path and thus conduction velocity is not known between the points used for triangulation. In addition, in the case of a rotor, activation sequences revolving around, or emanating symmetrically from, a core region may actually produce a net velocity of zero.

For these reasons, experts have stated that "no direct evidence of electrical rotors has been obtained in the human atria" in AF (Vaquero, Calvo et al. 2008). Thus, while it would be desirable to identify (and then locate) localized causes for human AF, this is not currently possible.

For human AF, particularly persistent AF, the absence of identified and located causes means that ablation is empiric and often involves damage to approximately 30-40% of the atrium that could theoretically be avoided if the cause(s) were identified and located for minimally invasive ablation and/or surgical therapy (Cox 2005).

Human VT or VF are significant causes of death that are poorly treated by medications (Myerburg and Castellanos 2006). Treatment currently involves placing an implantable cardioverter defibrillator (ICD) in patients at risk, yet there is increasing interest in using ablation to prevent repeated ICD shocks from VT/VF (Reddy, Reynolds et al. 2007). Identifying and locating causes for VT may be difficult and ablation is performed at specialized centers. In VF, animal data suggest that causes of VF lie at fixed regions near His-Purkinje tissue (Tabercaux, Walcott et al. 2007), but again this is very poorly understood in humans. The only prior descriptions of identifying and locating causes for VF required surgical exposure (Nash, Mourad et al. 2006) or were performed in hearts removed from the body after heart transplant (Masse, Downar et al. 2007)). Thus, minimally invasive ablation for VF focuses on identifying its triggers in rare cases (Knecht, Sacher et al. 2009) but cannot yet be performed in a wider population.

Existing sensing tools are also suboptimal for identifying and locating cause(s) for complex disorders such as AF, including single or multi-sensor designs exist (such as U.S. Pat. No. 5,848,972 by Triedman et al.). However, such tools typically have a limited field of view that is inadequate to identify causes for AF, that may lie anywhere in either atria and vary (Waldo and Feld 2008). Alternatively, they may require so many amplifiers for wide-area sampling that they are impractical for human use. Wide area sampling is advantageous and, in animals, is achieved by exposing the heart surgically (Ryu, Shroff et al. 2005) or removing it from the body (Skanes, Mandapati et al. 1998: Warren, Guha et al. 2003). In humans, even surgical studies only examine partial regions at any one time (for instance (Sahadevan. Ryu et al. 2004)), and introduce problems by exposing the heart to air, anesthesia and other agents that may alter the rhythm disorder from the form that occurs clinically.

Thus, prior methods have largely focused on mapping of the anatomy to identify whether a patient has a heart disorder, rather than determining the cause or source of the disorder. Thus, there is an urgent need for methods and tools to directly identify and locate causes for heart rhythm disorders in individual patients to enable curative therapy. This is particularly critical for AF and other complex rhythm disorders for which, ideally, a system would detect localized causes for ablation by minimally invasive, surgical or other methods.

BRIEF SUMMARY

The present invention discloses methods, systems and devices for identifying, locating and treating heart rhythm disorders. Locating and identifying the causes of the disorders enhances the ability to guide, select and apply curative therapy. In particular, the present, invention provides a method to identify and locate electrical rotors, focal beats and other causes for human AF and other heart rhythm disorders. Once identified, proper treatment may be applied to ameliorate and potentially eliminate the disorder, desirably using minimally invasive techniques as further described herein.

The present invention represents a significant advance over the prior art. For example, unlike the system and method described in U.S. Pat. No. 5,718,241, our invention identifies and locates causes (targets) for AF and other rhythm disorders, which may stay at approximately the same location within the heart for hours (see our example in a 47 year old man). Unlike the system disclosed in U.S. Pat. No. 6,847,839, the present invention is capable of finding sources that transiently appear or may move (they are "functional"), that may explain the variations in AF. Unlike the method described in U.S. Pat. No. 5,868,680, our invention directly identifies and locates cause(s) for a heart rhythm disorder, using as little as one activation event (beat) as shown in our examples. Unlike the method disclosed in U.S. Pat. No. 6,301,496, our invention directly identifies and locates electrical rotors, in which activation revolves around a core region, or focal beats, with activation radiating therefrom.

In one aspect of the invention there is provided a method for detecting and/or diagnosing one or more causes of a biological rhythm disorder, the method including the steps of: a) sensing biological activation signals at multiple locations using one or more sensors; b) collecting from said one or more sensors data which includes the sensor locations for each signal and the activation time of each signal; and c) analyzing said data to identify and locate the existence of one or more causes of said biological rhythm disorder.

In another aspect of the invention there is provided a system for detecting and/or treating one or more causes of a biological rhythm disorder, the system including: 1) sensor apparatus for sensing biological activation signals at multiple locations; and 2) a computer processor interfacing with said sensor apparatus for collecting and processing data received therefrom, said collected data including the sensor locations for each signal and the activation time or activation time duration of each signal wherein said processing includes ordering activation onset times at said sensor locations to create an activation trail indicative of a cause for said biological rhythm disorder. Software for performing the ordering, including an algorithm, may also be used.

In yet another aspect of the invention there is included a method for treating a biological rhythm disorder, the method including: a) sensing biological activation signals at multiple locations using one or more sensors; b) collecting from said one or more sensors data which includes the sensor locations for each signal and the activation time or activation time duration of each signal; c) analyzing said data to identify and locate the existence of one or more causes of said biological rhythm disorder, d) selecting one or more of said causes as indicating a primary cause of said biological rhythm disorder, and e) treating said primary cause to ameliorate or eliminate said biological rhythm disorder.

In another aspect of the invention there is provided a method for detecting and/or diagnosing one or more causes of a heart rhythm disorder, the method including the steps of: a) sensing heart activation signals at multiple locations using one or more sensors; b) collecting from said one or more sensors data which includes the sensor locations for each signal and the activation time of each signal; and c) analyzing said data to identify and locate the existence of one or more causes of said heart rhythm disorder.

In another aspect of the invention there is provided a system for detecting and/or treating one or more causes of a heart rhythm disorder, the system including: 1) sensor apparatus for sensing heart activation signals at multiple locations; and 2) a computer processor interfacing with said sensor apparatus for collecting and processing data received therefrom, said collected data including the sensor locations for each signal and the activation time or activation time duration of each signal wherein said processing includes ordering activation onset times at said sensor locations to create an activation trail indicative of a cause for said heart rhythm disorder. Software for performing the ordering, including an algorithm, may also be used.

In yet another aspect of the invention there is included a method for treating a heart rhythm disorder, the method including: a) sensing heart activation signals at multiple locations using one or more sensors; b) collecting from said one or more sensors data which includes the sensor locations for each signal and the activation time or activation time duration of each signal; c) analyzing said data to identify and locate the existence of one or more causes of said heart rhythm disorder; and d) selecting one or more of said causes as indicating a primary cause of said heart rhythm disorder; and e) treating said primary cause to ameliorate or eliminate said heart rhythm disorder.

In still a further aspect of the invention there is included an adjustable sensor device for sensing heart rhythm disorders, the device including: 1) a tubular shaft body having a first and second end; 2) an expandable sensor configuration attached to one end of said body, said sensor configuration including a plurality of intertwined sensor arms which, upon torsional movement, alters the spacing between the sensor arms, said sensor configuration being capable of contacting the luminal surface of a heart chamber when at least partially expanded; and 3) a retraction sheath for retaining and delivering said sensor configuration.

In yet another aspect of the invention there is provided an adjustable sensor device for sensing heart rhythm disorders, the device including: 1) a tubular shaft body having a first and second end; 2) a diametrically expandable spirally-shaped sensor configuration, which includes a plurality of sensors, said sensor configuration being capable of contacting the luminal surface of a heart chamber when at least partially expanded; and 3) a retraction sheath for retaining and delivering said sensor configuration.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The drawings constitute a part of this specification and include exemplary embodiments to the invention, which may be embodied in various forms. It is to be understood that in some instances various aspects of the invention may be shown exaggerated or enlarged to facilitate an understanding of the invention.

FIGS. 12A-12C show the results of using the method and system of the invention, to identify an electrical rotor in the right atrium.

DETAILED DESCRIPTION

Definitions

For purposes of this invention, the following definitions shall apply:

Detecting/Diagnosing: The terms detecting and diagnosing a rhythm disorder are used interchangeably in this application.

Activation time: For a given heart signal, this is the time of activation onset.

Figure 5:
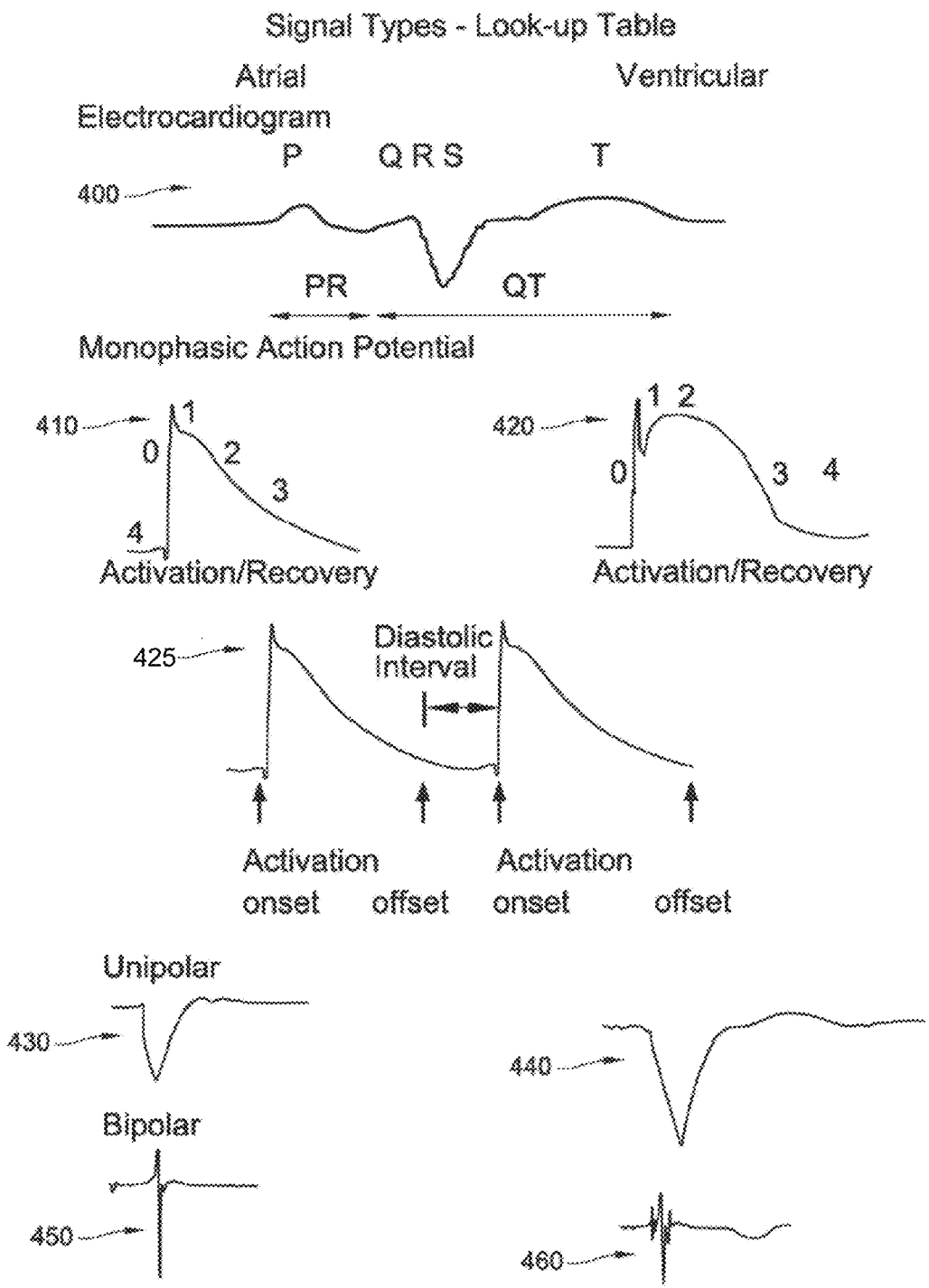
FIG. 5 illustrates some signal types from the heart to be analyzed by the invention, and defines some selected terms including activation onset, activation offset and diastolic interval.

Activation time duration: For the signal of a given heartbeat, the time period and the signal waveform between the times of activation onset and offset. Diastolic interval is the time period from activation offset of the prior beat to activation onset of the present beat (FIG. 5).

Activation trail: This is the ordering of the activation time onset at the sensor locations to create a discernible signature pattern, for example, including without limitation a rotational pattern around a core region indicative of a rotor, a radially emanating pattern from a core region, indicative of a focal beat cause, or a dispersed pattern, requiring further signal sampling and repeating of above analysis steps. Identify and locate: The process of discerning the presence of a localized or dispersed cause of the heart rhythm disorder, then locating said cause relative to sensor locations or relative to known anatomic positions in the heart. Heart rhythm disorder: An abnormal rhythm, often requiring treatment. These include without limitation, rapid rhythms of the top chambers of the heart (atria) such as rapid and abnormal activation of the normal sinus node (inappropriate sinus tachycardia or sinus node reentry), atrial tachycardia (AT), supraventricular tachycardia (SVT), atrial flutter (AFL), premature atrial complexes/beats (PAC) and the complex rhythms of atrial fibrillation (AF) and certain forms of atypical atrial flutter. Rapid rhythms can also occur in the bottom chambers of the heart (ventricles), including such as ventricular tachycardia (VT), ventricular fibrillation (VF), torsades de pointes and premature ventricular complexes/beats (PVC). Heart rhythm disorders can also be slow, including sinus bradycardia, ectopic atrial bradycardia junctional bradycardia, atrioventricular block and idioventricular rhythm. Cause of biological or heart rhythm disorder: This term is used interchangeably with "source" of the biological or heart rhythm disorder in this application. It refers to, without limitation, a rotational pattern of activation sequence around a core region indicative of a rotor, a radially emanating pattern from a core region indicative of a focal beat cause, or a dispersed pattern. In this invention, when a dispersed cause is found, signal sampling is extended to additional multiple locations and the detection and analysis steps of the invention are repeated. These causes are directly responsible for the perpetuation of the heart rhythm disorder. Sensor: This term is used interchangeably with electrode in this application. It refers to an apparatus for detecting and transmitting signals from the heart or to the heart.

Prior to the discovery of the present invention, the causes of human biological rhythm disorders, and particularly heart rhythm disorders, had not been identified. The present invention represents the first known instance where a method of detecting, diagnosing and subsequently effectively treating, in an accurate and minimally invasive manner, the cause(s) that sustain, perpetuate, or "drive" human biological disorders has been described. This method enables the physician to target these sources for modification or elimination to abolish the disorder. Although one preferred embodiment is for minimally invasive procedures for heart rhythm disorders, the invention can also be applied to surgical therapy, and for disorders of electrical impulse generation or propagation in organs such as the brain, central nervous system (where it may locate causes of epilepsy or seizure), peripheral nervous system (where it may detect tumors), skeletal muscle and smooth muscle such as the gastrointestinal tract, bladder and uterus.

In accordance with an embodiment of the invention, there is disclosed an apparatus to sample signals, for example a sensor device such as an electrode catheter from multiple locations within a human organ, such as the human heart, at varying spatial resolutions and fields of view and with apparatus to alter the number of sensing channels accordingly.

In accordance with an embodiment of the invention, there is disclosed a method to identify and localize electrical rotors, focal beats and other localized causes for heart rhythms, including complex rhythms such as AF. VF and polymorphic VT.

Embodiments of the invention may use processes and software methods such as ordering the activation sequence to create an activation trail, processes such as the Hilbert transform, other phase delay methods, spatial coherence analysis and other methods.

In one embodiment of the invention, data collected from sensors and analyzed is stored as data in a database that is automatically updated. This database is used to assist the physician in the diagnosis/detection of localized causes, or to classify a pattern of causes of rhythm disorders. This may take the form of a probability distribution map of causes in patients with specific characteristics.

In accordance with another embodiment of the invention, there is provided an apparatus to display causes for the biological rhythm in a format that can assist the physician in treatment. For example, a visual display screen may be connected to a processor to allow for viewing of the activation trail and to allow for visual location of the core of a rotor, focal source or other cause of the disorder. Audio formats may also be used alone or in combination with the visual format. For example, in addition to or instead of the visual depiction of the source such that the core can be visually identified, the coordinates of the source and its core can be provided to the user by audio indications as to the location and cause of the disorder. Visual depiction is particularly desirable because it provides the practitioner with a clear representation of the cause and provides a reference for identifying the core of the cause, which greatly facilitates the selection of treatments. For example, a visual representation of the actual rotor or focal beat allows the practitioner to accurately determine where to direct the ablation catheter or other treatment.

In accordance with another embodiment of the invention, once the cause of the disorder is identified, use of a treatment device or method, to modify or destroy the site of an identified and localized source may be employed to treat or eliminate the rhythm disorder. Non-limiting examples of treatment devices and methods include the use of destructive energy (ablation) such as by ablation catheters, surgical ablation methods, surgical removal or using devices inside the heart such as implanted leads or other physical device, stimulating energy (pacing), direct delivery of pharmacologic agents, cellular therapy or other intervention techniques. In one embodiment, a catheter capable of sensing signals from the body, and particularly from the heart, may also include a means of treatment, such as the ability to delivery ablation energy, stimulation energy, drug therapy, cellular therapy such as stem cells or gene therapy, or other treatment means. Thus, such a catheter may be employed both in the detection and in the treatment of the disorder.

The present invention is particularly suited for the detection, diagnosis and treatment of complex heart rhythm disorders such as, for example, VF, polymorphic VT, torsade de pointes and AF, where once the localized cause is accurately identified and pinpointed, accurate and targeted ablation of the localized cause may be implemented. As discussed above, identification and physical location of the cause was previously not possible, and hence extraordinarily difficult even for experienced practitioners to treat successfully, much less substantially ameliorate or eliminate.

In addition to finding the cause of and subsequently treating complex heart rhythm disorders, the present invention may also be applied to help diagnose and treat 'simple' rhythms that emanate from a single site by accelerating and simplifying analysis for the practitioner. For heart rhythm disorders, such simple disorders include focal atrial tachycardias, multifocal atrial tachycardias (MAT), sinus nodal reentry or inappropriate sinus tachycardia, ventricular tachycardia (VT), premature atrial complexes (PACs) and premature ventricular complexes (PVCs).

Included in the invention are a process and system to collect data, including sensing devices and recording systems The collected data includes at least the location of each sensor which transmitted one or more signals and the onset time at which each activation signal or activation time duration occurred. The processor receives this information and sequentially orders the activation onset times. The result of this computation is the creation of an activation trail which creates a signature pattern for the disorder and indicates both the location and the type of the cause to the disorder, i.e., whether it is a rotor, focal source or a dispersed pattern, i.e., no localized source, hence requiring further data to be collected from a different area of the heart or other body region. The data once ordered in this manner creates an activation trail which can visually be depicted on a visual display to show, in the case of a rotor source, the actual rotational pattern of the rotor such that the core of the rotor is visually apparent and can easily be identified and hence treated. The same hold true for the depiction of a radially emanating source, such as a focal beat. The sequential ordering of the activation onset times at each sensor permits the location of focal rhythm disorders, such that the focal core can be easily located on the visual display for targeted and accurate treatment. Desirably, the rhythm sources or causes are displayed over a period of time to allow the practitioner to fully observe the causal point or area and to make a comfortable assessment as to the appropriate treatment at the causal location. In one embodiment the data and/or the visual displays of the processed data (i.e., a "movie" of the activation trail) elucidates the signature pattern of the cause of the rhythm disorder. Such stored information allows for the practitioner to consult previous patterns to aid in improving the identification, localization and treatment of similar causes. In some instances, such stored information allows for extrapolation of measured real-time data to provide predictive models or to clarify certain measured patterns using similar known patterns.

A further embodiment of the invention provides a process and system for the treatment of such causes, often by modification or destruction of tissue where causes reside. Sixth, a preferred embodiment enables the invention to be used in an "offline", non-real-time review mode, rather than directly during a procedure to treat a patient.

The process and system of the invention may be employed to localize sources (i.e., find the physical location of the cause) for abnormal electrical impulse generation or propagation in the brain or central nervous system using the electroencephalogram or other index to guide invasive therapy (surgery) or external beam irradiation to identify and treat seizure or epileptic foci, or focal tumors (malignant or otherwise). The invention may also be used to identify sources for abnormal impulse propagation in striated muscle (such as injury in skeletal muscle), the gastrointestinal system (such as esophageal spasm), the urogenital and respiratory systems. The invention may also be used to detect tumors (malignant or otherwise) in any body system. The invention also has applications outside of medicine, such as for locating the source of a seismic event or for locating energy sources in tandem with methods such as radar or sonar.

The invention has several aspects to its process and system for carrying out the process. By way of example and not of limitation, in one aspect of the invention, signals are detected from multiple locations in an organ in the rhythm disorder, altering the spacing between sensors to optimize clarity of said sensing. A particularly desirable embodiment also records these signals from a heart, or other body part, during a rhythm disorder and stores them in a data base. The location of each sensor associated with a particular signal, as well as the activation onset times at each sensor are transmitted to a processor for analysis including sequential ordering to form the activation trail identifying the cause of the disorder and its specific location in the body. Creating a database of causes, which may be manually or automatically updated allows for accessing the data base to assist in the identification and localization of disorder causes. This is used when data collection in the current patient is of limited quality, to compare the pattern in a patient to prior recorded rhythms in the patient to determine if the rhythm is the same or different, or to compare the pattern in a patient to that from another patient, such as one with similar clinical characteristics. Previously stored data from a previous case may be used to help identify, localize and display causes for the rhythm disorder in a present case.

Visually displaying the sources of the disorder is extremely useful to the practitioner because it serves as a visual guide to the existence and location of the cause, and permits subsequent targeted and accurate treatment to ameliorate or eliminate the rhythm disorder.

In other aspects of the invention, previously stored data from another case may be used to identify, localize and display causes for the rhythm disorder in a present case. This can then be used to plan the use of this invention in a future procedure.

Description of Useful Components (Modules) and Devices

Figure 1:
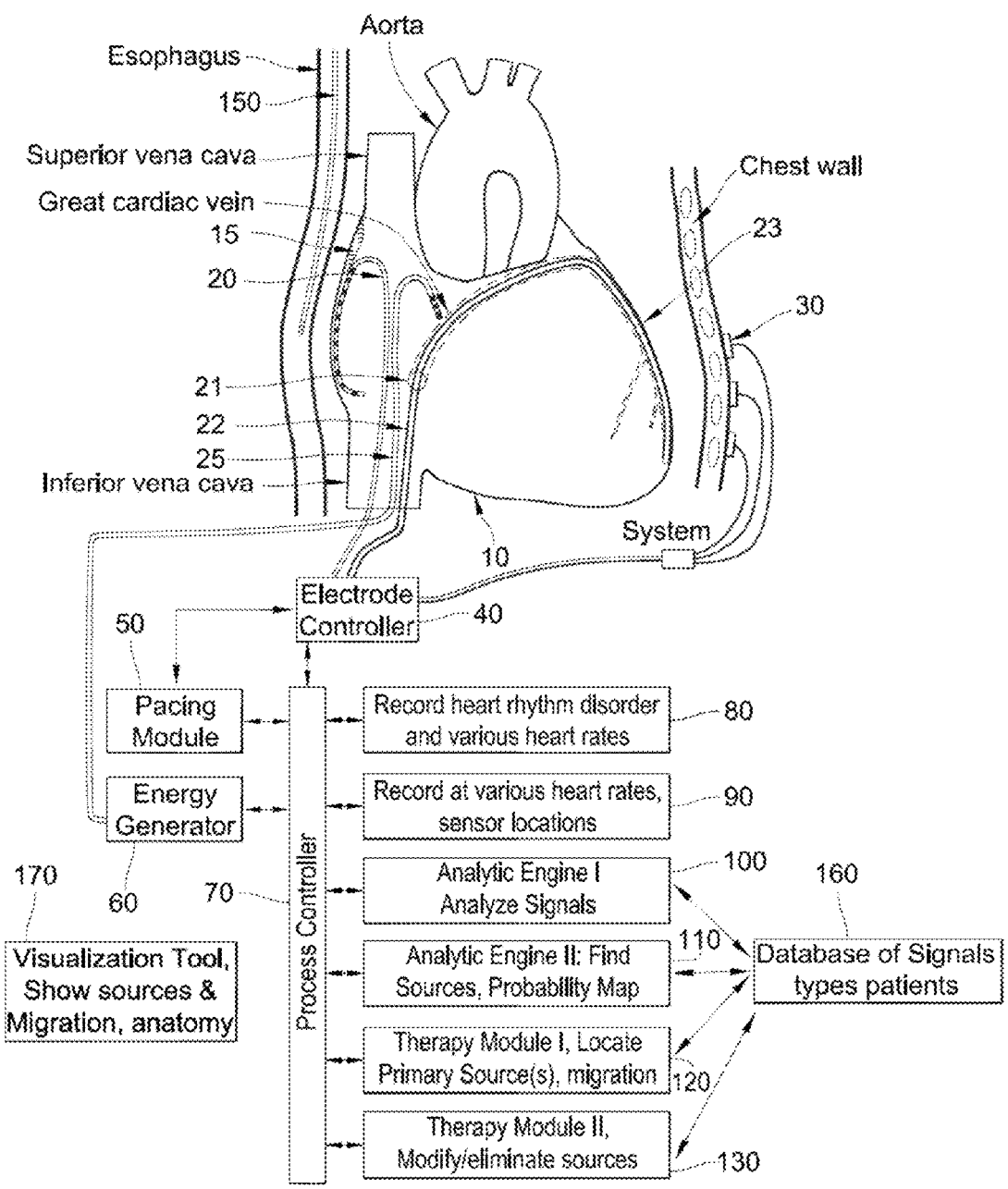
FIG. 1 is a depiction of the heart showing the use of sensors, ablation catheter and the electronic processing components of the present invention which processes signals from the heart and orders them in accordance with the invention.

FIG. 1 shows a schematic of various useful components (modules) which may be used in the process and system of the invention. The modules may be separate from each other and cooperatively interfaced to provide their function, or one or more of them may be integrated with each other of contained in the processor, such that the system has less separate hardware units. FIG. 1 depicts an embodiment which allows a cause of the disorder to be localized during a minimally invasive percutaneous procedure, or other procedures such as using surface ECG, a magnetocardiogram, an echocardiographic and/or Doppler measurements from ultrasound, electromagnetic radiation, sound waves, microwaves, or electrical impedance changes.

In FIG. 1, electrical events in the heart 10 are recorded with sensing electrodes. These electrodes may be catheters 20 placed within the chambers or vasculature of the heart, including custom-designed recording catheters exemplified in FIGS. 2-4, The electrodes may also be extensions of leads from an implanted pacemaker or cardioverter-defibrillator, catheters used to record monophasic action potentials or other signals, that typically arrive via the vena cavae or coronary sinus 22. Thus, although particularly useful in the invention, the process and system of the invention need not, however, employ the specialized catheters of FIGS. 2-4, as any catheters or sensing devices used inside or outside of the body which capable of accurately transmitting the activation times and location of their occurrence may be employed.

Electrodes 23 may record from the epicardial or pericardial surface of the heart, accessed via electrodes 21 in the coronary sinus, via the electrodes 23 in the pericardial space or other routes. Electrodes may be located in proximity to the nerves supplying the heart 15, which may be located in the left atrium and ventricles. Electrodes may be virtual (computed) electrodes from a computerized mapping system, routine or high-resolution ECG mapping electrodes 30, electrodes implanted under or on the skin, or derived from methods to non-invasively detect signals without directly contacting the heart or body. Electrode information may also be derived from stored electrograms in a database 160.

An electrode 25 placed near the heart may be used to modify or destroy regions that are near or at the cause(s) for a rhythm disorder. If the electrode is an ablation catheter, it interfaces to an energy generator 60. Other electrodes may interface with a controller 40, and a pacing module 50, and all desirably communicate with a process controller 70. Ablation or pacing can be directed to nerves supplying the heart 15, which are located at many locations of the heart. Internal ablation electrodes may be replaced with an external ablation system, such as external probes during surgery, or as in external focused irradiation or photon beam as for cancer therapy. In addition, modification of sources, i.e., treatment of the causes of the disorder, may be achieved by delivering appropriate pharmaceutical compositions, gene therapy, cell therapy, or by excluding tissue (at surgery or by using specialized devices).

The process controller 70 may include various components or modules. On such component or module includes a sampling module 80 which is capable of recording signals during the rhythm disorder, recording at various rates not in the rhythm disorder (by pacing), and/or recording during rates that simulate the heart rhythm disorder (by pacing or other methods). Signal amplifiers (not shown) may be used to enhance the signal clarity and strength, and the process controller may also intelligently assign the fewest number of recording amplifiers to sense from a sufficient number of locations to identify and localize the cause. For instance, the system may use only 50-60 physical amplifier channels to record from 128 sensors (for example, from two commercially available multipolar catheters), by recording those 128 sensors on a "time-share" basis by time-slicing, or by activating individual/multiple sensors close to a rhythm cause while deactivating others. This "switching" functionality may be performed by a switching component that connects the sensor device with the electronic control system, and that may be embodied in one or more other components. Switching may be manual or automatic, determined for instance on where causes of the heart rhythm disorder lie. Module 90 interfaces with the pacing module to provide additional heart rates for sensing the biosignal. This is particularly useful for the non-real time mode (mode 6), described herein, because it can study the heart at different heart rates even when not in the particular heart rhythm disorder being diagnosed and treated.

The inventive method and system processes the collected data using analytical methods, which may be performed by analytic modules. For example, in FIG. 1, Module 100 is part I of an "Analytic Engine." This portion of the Analytic engine determines the onset and offset for the biologic signal over time, at each sensed location. This is implemented by creating a series of activation times (onset timing) and recovery times (offset timing) during the rhythm over time (illustrated in FIG. 6). The signal is typically represented as voltage over time (that is, as a voltage-time series). Activation time can be processed in many ways. The simplest includes manual assignment at each location. Automated or calculated assignment can be achieved by using zero of the first derivative to define maxima or minima, zero of the second derivative to indicate maximum upstroke or downstroke, or similar methods. Activation onset and offset times can also be assigned when the voltage time-series crosses a threshold. Another possible method to assign activation times is using pattern-matching. For instance, a pattern selected to represent the activation duration can be correlated to the signal at multiple time points over time. The time when said correlation values are high indicate recurrences of said template, and thus are considered activation times. The template used for this analysis can also be obtained from stored data in a database, or computed from a rate estimate for the rhythm at that location. Simultaneous recordings from multiple sensors can help in analyzing activation, particularly for complex rhythms such as AF or VF when signal quality may be noisy, of poor quality or show multiple components at different times. From simultaneous recordings, a reference signal is selected, preferably at a nearby location to the channel being analyzed. Signals on the reference channel are used to select signal or signal components on the channel being analyzed. This can be done by using components that retain a similar timing over time, using pattern matching or correlation functions, vectorial analysis or other methods. If many methods are required, heuristics, pattern recognition methods, and so-called "fuzzy logic" approaches can be applied, constrained by known pathophysiology of the atrium.

Module 110 is part II of the Analytic Engine that actually computes and localizes. i.e., determines the existence and location of sources (causes) for the heart rhythm disorder.

Some embodiments of the invention include a "Therapy Engine," which may contain one of more modules designed to cooperatively perform different functions in the system and process. For example, module 120 in FIG. 1 may be responsible for determining the location and migration pattern of sources for the rhythm disorder within the heart. This may be a first module of the Therapy Engine, and is used to compute the location and spatial region which is required to be modified in order to treat or eliminate the rhythm disorder. Treatment may be by delivery of ablation energy or other means as discussed herein, and is not simply one point or region if the source migrates during ablation. Module 130 is representative of another module of the Therapy Engine, and desirably directly interfaces with the energy generator to ablate (destroy), modify (ablate or pace) or stimulate (pace) tissue at sites likely to represent sources. Alternatively, the Module 130 may be used to modify tissue without destructive energy, for example by delivering pharmaceutical agents, or gene or cellular therapies.

Module 170 of the system shown in FIG. 1 is representative of a tool to display the identification or location of causes visually or in auditory fashion, to assist the physician in treating or eliminating the rhythm disorder. For example, this module may include a display screen which permits the textual, graphic and/or auditory visualization on the screen of the rotor, focal or other cause of the disorder to be clearly seen by the practitioner. In some embodiments, a "movie" clip of the disorder found will be presented on the screen. This clip is a real-time presentation of the actual cause and location of the disorder. For example, once the analysis of the data has been performed in accordance with the process of the invention, i.e., the location of the signals and their activation onset times have been sequentially ordered, the result of this analysis and computation will be shown on the screen in the form of an activation trail. If the pattern of the activation trail signifies a series of activations revolving around a central core, then a rotor has been found and is in fact a cause of the disorder. Similarly, if the pattern of the activation trail signifies a series of activations which emanate radially from a central core region, then a focal beat has been found and is in fact a cause of the disorder. Thus, the inventive process permits the direct finding of the cause of the disorder and the convenient visualization of the existence, type and location of the disorder for the practitioner. In the event that no discernable pattern is found, i.e., the activation trail is not localized, then additional signal sampling by moving the sensor locations and/or turning-on already placed sensors may be appropriate. The additional signal samples may then be processed in accordance with the invention and shown on the screen. If a cause is found via the additional sampling and processing of the data, then a decision as to the appropriate treatment may be made. In the event that a dispersed activation trail and pattern is found, further additional sampling may be advisable until such time as the practitioner feels is sufficient. In some instances, the result of the process will render a finding of the existence and location of a rotor or a radially emanating focus. In other instances, where a dispersed pattern remains even after repeated sampling and processing, a diagnosis may be made ruling out a rotor or focal beats as the cause. Thus, the finding of a rotor or a focal point (beat) will be essentially a detection and diagnosis concurrently, whereas the lack of such a finding will be a diagnosis which may rule out the presence of either of these causes of the disorder.

Mode 1 Signal Sampling (FIG. 1. Reference 80)

Signal sampling can be done in real time, during a procedure to ablate or treat the rhythm disorder, beforehand to plan for a procedure, or afterwards to review the disorder. As stated above, signals are collected at one or more locations from the organ using a variety of sensor types. Contact sensors should maintain as good a contact with the tissue as possible. In the preferred mode, electrodes should record at multiple sites simultaneously or nearly simultaneously. The fastest heart rhythm disorders such as AF have cycle lengths >100 ms, so that signal acquisition for substantially less than this time is considered 'nearly simultaneous'. An alternative mode of operation allows moving a sensor to sequential sites. The invention may be used with any existing sensor apparatus.

Figure 2:
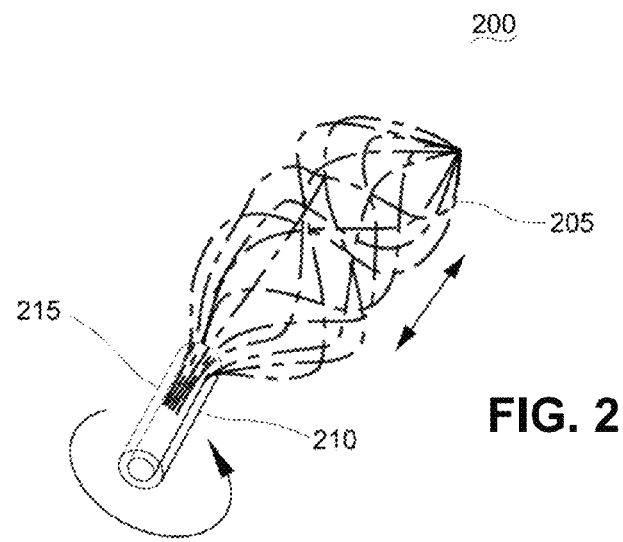
FIG. 2 shows a sensor apparatus design of the present invention that detects biosignals for a wide area of the heart chamber at low resolution, then for a narrower area at higher resolution.
Figure 3:
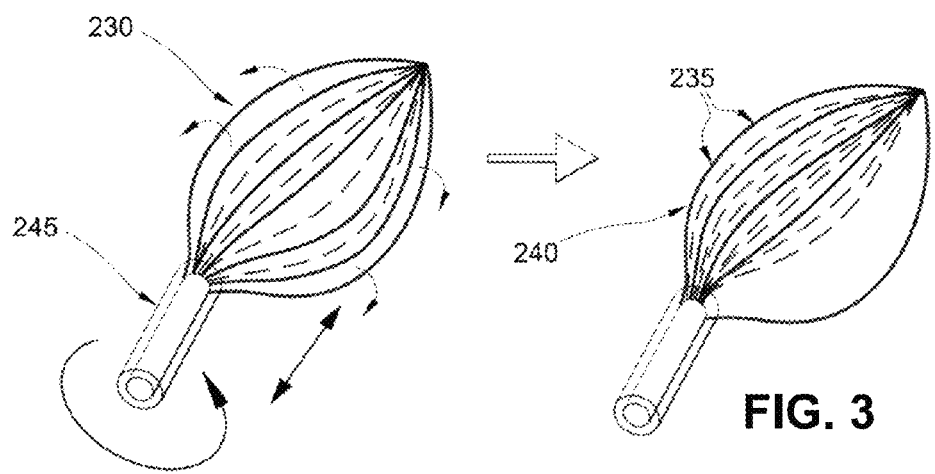
FIG. 3 shows another sensor apparatus design of the present invention that detects biosignals for a wide area of the heart chamber at low resolution, then for a narrower area at higher resolution.
Figure 4:
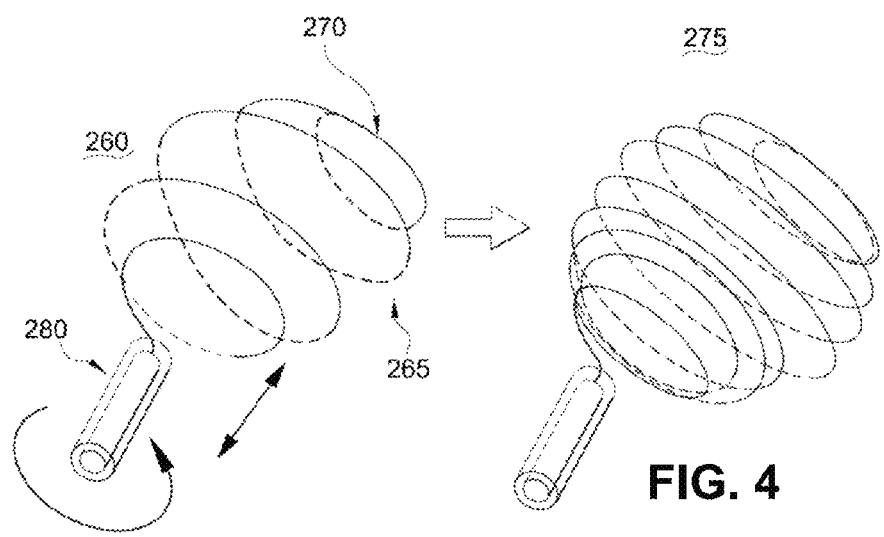
FIG. 4 shows another sensor apparatus design of the present invention that detects biosignals for a wide area of the heart chamber at low resolution, then for a narrower area at higher resolution.

Although a variety of commercially available electrode devices may be used to obtain signal sampling, particularly useful device embodiments for signal sampling are shown in FIGS. 2-4. These apparatuses use multiple sensors that may be individually activated or deactivated, or moved relative to one another. This enables adaptive spatial resolution, in that sensor spacing can be increased or decreased as desired. Widely-spaced sensors provide a wide field of view to 'survey' the rhythm for a large portion of the organ (e.g. left atrium of the heart). Once the source location is approximated, the configuration is desirably altered to reduce sensor spacing for higher spatial resolution over a narrow field of view. A tightly spaced sensor configuration is preferred for applying energy to a focused region to treat a source.

Adaptive spatial resolution is an important advantage of various embodiments of the present invention. This can be achieved by physically moving sensors. FIG. 2 shows concentric helices (element 200), with multiple sensing elements (electrodes or probes) for sensing signals and in some instances delivering energy or other treatment therapy (element 205). The helices are widely spaced when parts of the catheter remains non-deployed (element 210) inside the shaft (element 215). Rotating and advancing the assembly introduces more probes in the chamber, and reduces their spacing. FIG. 3 another embodiment of an inventive sensor catheter in the form of an adjustable fan catheter, with multiple meridians (element 230) each containing multiple sensing elements (electrodes or probes) (elements 240), also for sensing and in some instances for delivering energy or other treatment therapy. By a combination of twisting or torsional motion along the shaft axis (element 245), as depicted in the figures, the meridians may be more widely spaced (element 230) or more closely spaced (element 235), i.e., spatially adjusted. FIG. 4 shows another embodiment of an inventive sensor catheter in the form of an adjustable corkscrew design, with a small number of spiral meridians (element 260) ending on a blunt non-traumatic end (element 270). As with the design structures of FIGS. 2 and 3, the meridians of FIG. 4 may include multiple elements (electrodes or probes) (elements 265). The corkscrew can be advanced or retracted into the sheath by manipulating the shaft (element 280), to increase or decrease the corkscrew size and/or probe spacing. These designs can be made larger or smaller to fit a larger or smaller organ (e.g., atria of varying sizes), or substructures including pulmonary veins or the superior vena cava that may be sources for rhythms such as AF. Physical movement can be achieved manually by the physician or automatically by using machines. Given the observed properties of sources for heart rhythm disorders, it is desirable that the sensors sense from at least about 25% of the surface area of each one or more chambers of the heart. These designs are illustrative only, and are not intended to limit the actual physical design or application of this invention.

Optimal contact for each sensor can be monitored by the process controller 70 for adequacy in various ways. For example, the process controller 70 can verify contact via stability in the amplitude of sensed signals. Alternatively, the process controller 70 can condition the pacing module 50 to emit signals through electrodes 20-30, and use the amplitude of evoked responses to verify contact. As a third alternative, the processing controller 70 can determine contact by confirming stable tissue impedance (in AF, for instance, where pacing is not possible). As other alternatives, catheters designed to examine mild injury patterns, or designed to directly measure contact force, can be used. In addition, catheter manipulation can be controlled robotically in semi-automated or automated fashion, as well as manually.

Adaptive spatial resolution can also be achieved electronically. Sensors in this adjustable sensor device are connected to an electronic control system that may activate or deactivate individual sensors. This may be performed manually, such as if the physician wishes only to focus on one region of the organ, or automatically by the process controller in FIG. 1 to focus on a region determined to be where the heart rhythm source lies. An electronic switching apparatus controls independent switching of connections between the sensors and electronic control system, in order to maximize use of a practical number of amplifier channels. These electronic components may be embodied by various combinations of traditional (wired) electrodes, fiber optics, etched-wafer circuit designs, biologic sensors, chemical sensors, pharmaceutical sensors, piezoelectric sensors, infrared sensors, patient-compliant optical imaging, optrodes, remote sensors and other designs.

Electronic switching may also be achieved by time-slicing. A large number of locations may need to be sensed, but the number of sensing channels may be limited. Signal time-slicing can record a larger number of sensing channels from a smaller number of channels. For instance, signals are often sampled every 1 ms (at 1 kHz) although data acquired every 10 milliseconds (ms) or so is often sufficient for AF or VF source analysis. Thus, the system can sense at location 1 for 3 ms, locations 2 and 3 for 3 ms each, then return to sensor 1 to repeat the cycle at the 10 ms time point. In this way, 90 locations can be sensed using 30 channels. Any appropriate configuration can be used, depending on the switching time in hardware or software, and allowing for noise factors when switching between channels. Many other methods can be used to increase the effective number of channels, including sending multiplexed signals along a fiber optic or other device, or storing signals in random access memory then using off-line analysis to amplify and analyze each in turn.

Numbers of sensed locations can also be increased using a combination of sensors lying in contact with different heart planes. For instance, electrodes on the endocardial (inner) surface of the heart may be complemented by electrodes on the epicardial (outer) surface and possibly those in the heart muscle itself (via implanted electrodes) to increase overall spatial resolution. This is of particular value in the atrium, whose wall is thin and where epicardial and endocardial electrodes may target similar regions. In the ventricle, or in thick walled regions of the atrium, different planes may provide different information.

In certain preferred embodiments, sensing can be performed using one or more sensors (probes) moved sequentially within the organ during the heart rhythm disorder. When a single probe is used, signals from each location are aligned relative to a timing signal fiducial. This method is easy to apply when a rhythm is relatively regular within the heart, such as the 'simple' disorders of focal atrial tachycardia or atrial flutter. However, this method can also be used as an approximate guide if the rhythm is irregular within the heart, such as the complex rhythms of AF or VF. This has the advantage of requiring fewer sensors, and will work if sources show some stability in space. For instance, while AF is irregular, activation may be regular at localized sources, for example at certain locations such as near the pulmonary veins.

One particularly useful embodiment for using sequential sensing at multiple locations is now illustrated for a moving probe with two sensors (such as the two bipoles of a clinical quadripolar catheter), although more sensors may be applied if available. At each location, one sensor is considered the reference and the onset times for successive cycles (beats) are fiducials. The difference in activation time at the second sensor is used to indicate relative timing. The probe is now moved so that one sensor overlies the previously sensed location. The second sensor now senses a fresh location and can record relative timing onsets for multiple beats here. The process is repeated for the entire region of interest. Because this process introduces stability in relative timing between locations, variability can be reintroduced stochastically using observed beat-to-beat timing variations at each location.

An alternative approach is to use gradients in rate and/or organization within the chamber, compared to stored data from a database for that rhythm (including AF or VF). After sensing sequential locations, the activation rate in both chambers is compared to stored patterns that describe this relationship at various sources (rotors or focal beats) and surrounding sites. An error-minimization approach (such as least-square-errors) may be used to estimate the source location. Estimates may be refined adaptively, based on similarity to subsets of stored patterns and using algorithmic, heuristic, fuzzy logic or other pattern recognition scheme. This process is repeated iteratively. For a spatially consistent source, second and subsequent iterations will add precision to the original estimate, and may be focused at locations closest to the estimated source.

Delivery of treatment therapy may be another feature of the sensor device, that will be described in detail later herein.

Mode 2 Computing Causes of Heart Rhythm Disorders

The first step in analysis is to determine the signal type, using a lookup table as illustrated in FIG. 5, reference numerals 400-460. This step determines if the signal arises from the heart (cardiac), brain, respiratory system, gastrointestinal tract, urogenital system, and so on. If cardiac, the signal may be a surface ECG, intracardiac, echocardiographic or other signal. If intracardiac, the signal is further classified as an action potential (monophasic action potential), bipolar electrogram, unipolar electrogram or other. Some of these signals provide high quality information (e.g. monophasic action potential recordings in the heart), while others do not. Lower quality signals are more likely to require pre-processing, filtering, averaging, comparison against stored signals in a database, in that patient at different times and other computational steps to allow source localization.

Figure 6:
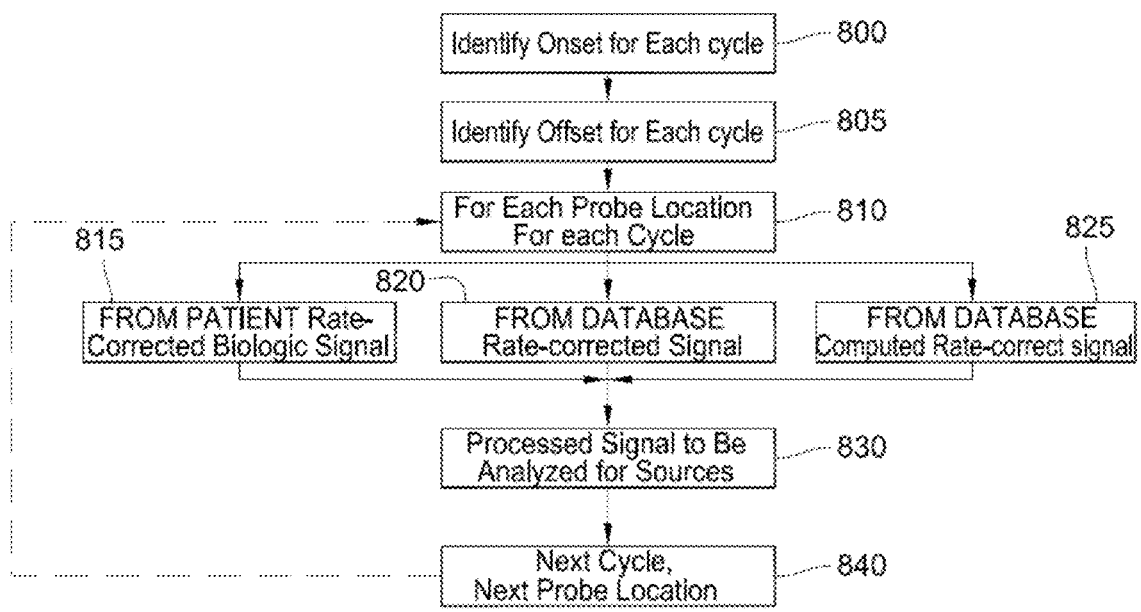
FIG. 6 is a flowchart showing analysis of signals at multiple locations to identify and locate causes for biological rhythm disorders in accordance with the present invention.

In FIG. 6, the signal is parsed between steps 800-840 to identify its type in the lookup table (from FIG. 5). This includes assigning activation onset and offset, and the interval between beats (diastolic interval) that depends upon the signal type illustrated in the lookup table in FIG. 5. The lookup table can be a comprehensive biosignal inventory, with data on the distinct physiological role of each component for computational purposes. Components may vary with rate and may fluctuate from beat to beat. Each signal component may reflect a distinct aspect of normal or abnormal physiology and thus indicate likelihood that the rhythm disorder may arise. Examples are not intended to limit the scope of the lookup table, which may include signals from other muscles (e.g. skeletal muscle, bladder and gastrointestinal tract), the brain and the nervous system.

The next step in analysis is to define, for each sensed location, the physiological signal to be analyzed. The goal is that the resulting signal best represents actual physiological activation and recovery occurring in the heart rhythm disorder at each location. When the recorded signal is "clean" (has a high signal-to-noise ratio), this will be the physiological signal. If signals are noisy, then filtering, noise reduction and other schemes may be needed to reveal the physiological signal. Said noise schemes may require recording while the patient holds his/her breath for several seconds. For analysis of atrial rhythm disorders, the physiological signal is best recorded between ventricular activations (in the R-R interval), that may be facilitated if the heart beat is reduced (R-R interval is prolonged) using agents to slow ventricular rate or by reducing pacemaker rate in patients with such devices.

Figure 7A:
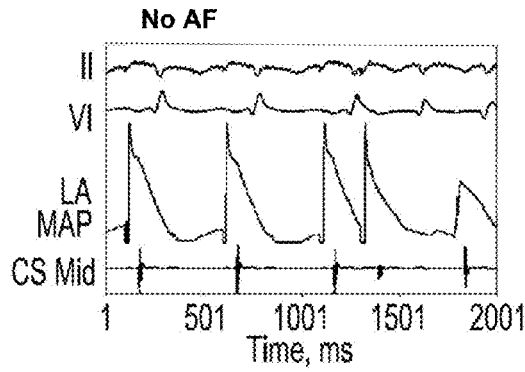
FIGS. 7A-7G illustrate examples of computation of rate-behavior (restitution) curves for human signals, with insertion of physiological patterns in some cases.
Figure 7B:
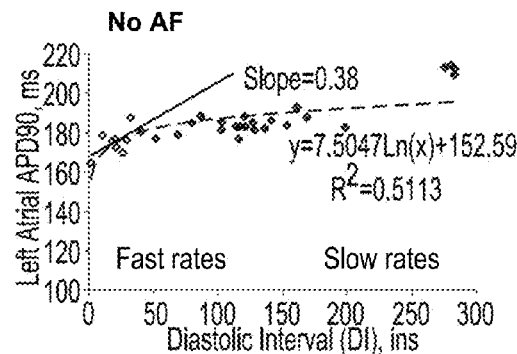
Figure 7C:
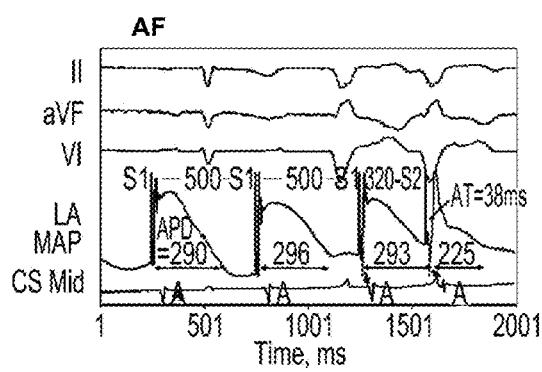
Figure 7D:
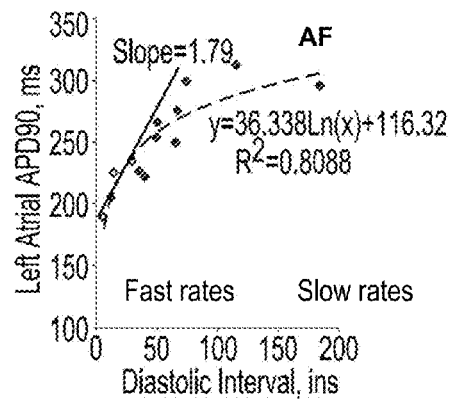
Figure 7E:
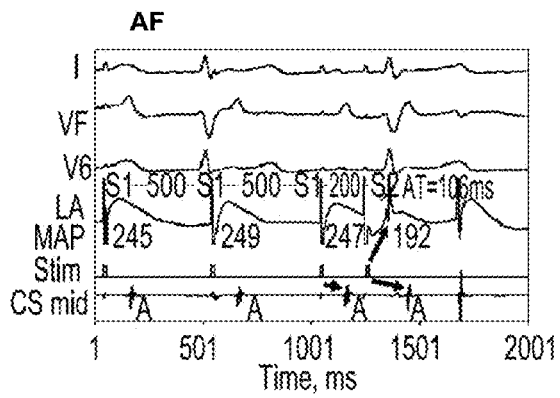
Figure 7F:
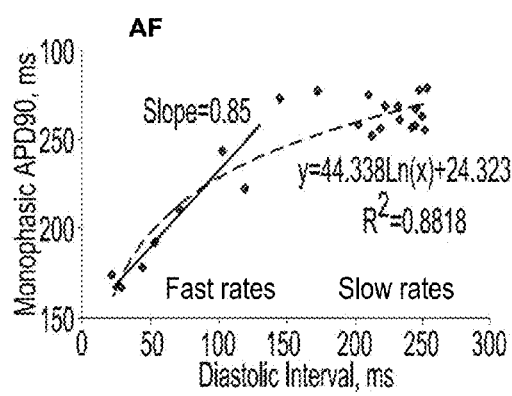

FIGS. 7A-7G illustrate a particularly useful embodiment for constructing physiological signals using computational methods to compensate for limitations due to noisy or low quality data. First, the response to rate of for each signal type (monophasic action potentials, MAP, illustrated in FIGS. 7A (patient without AF), 7C (AF patient) and 7E (AF patient)) is determined. This is performed by sensing signals at varying rates when in the rhythm disorder, or when not in the rhythm disorder (such as by pacing, see mode 6, discussed below). The response of the signal duration (illustrated for MAP) to varying rate is shown in panels FIGS. 7B, 7D and 7F. FIG. 7B (no AF) shows no shortening with rate, while, with AF, FIGS. 7D and 7F show that MAP shortens at increasing rate (that is, when diastolic interval shortens). It is to be noted that the response to the same set of rates may vary when the patient is and is not in the heart rhythm disorder. FIGS. 8A-8E show this. Pacing with delivery of a single extra beat in FIG. 8A results in the restitution plot shown in FIG. 8B as soon as AF begins. However, after several minutes, the restitution curve changes as shown in FIGS. 8C-8E.

Figure 7G:
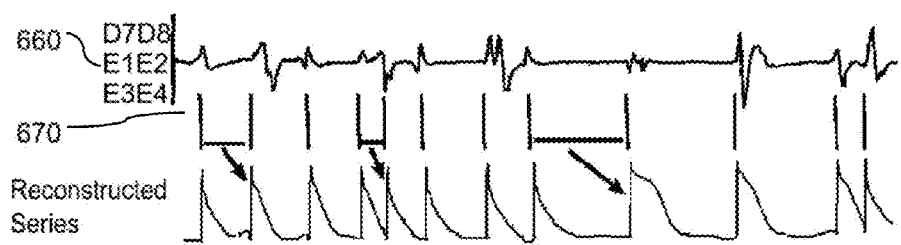
Figure 8A:
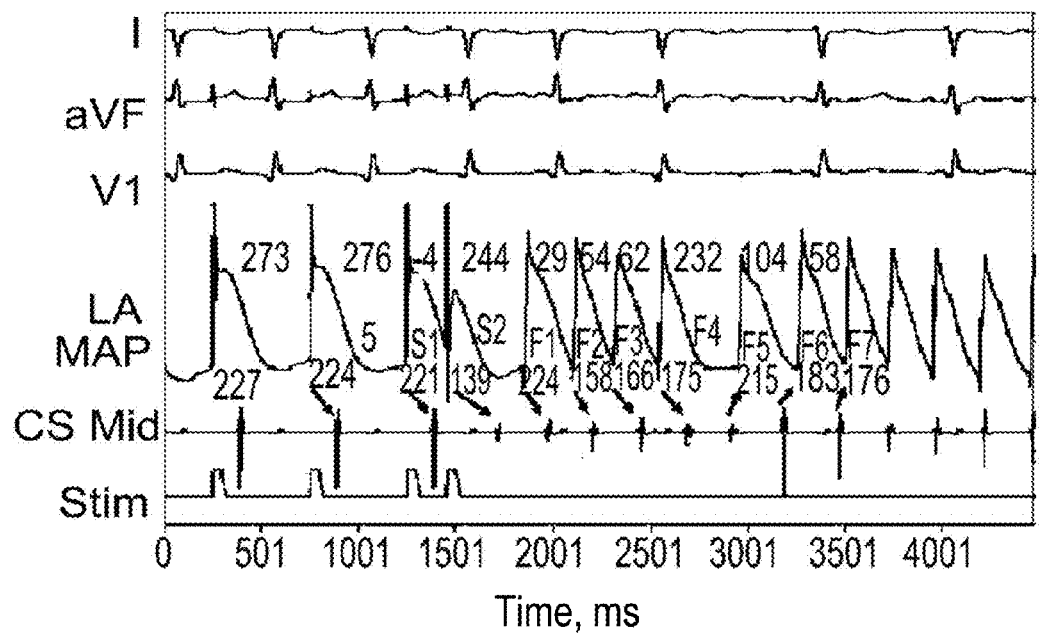
FIGS. 8A-8E illustrate that rate-response (restitution) of human monophasic action potential duration may differ when measured between paced rhythms and AF.
Figure 8B:
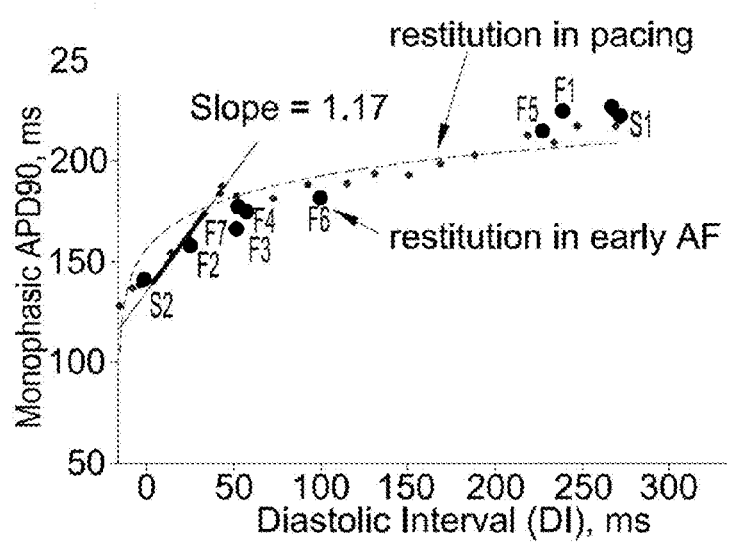
Figure 8C:
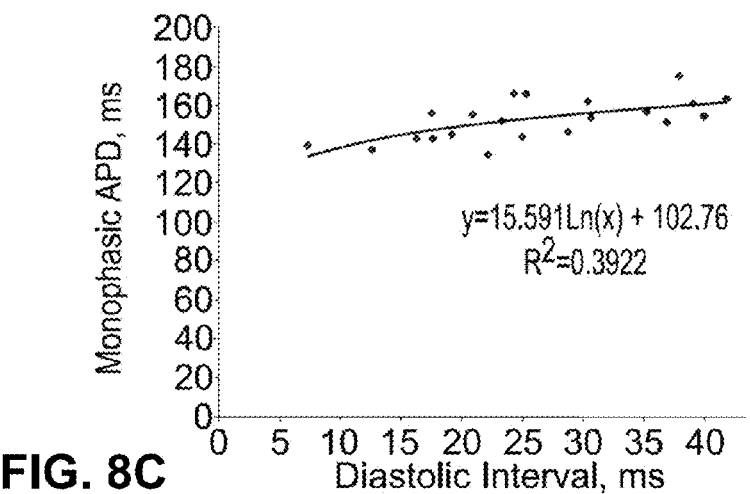
Figure 8D:
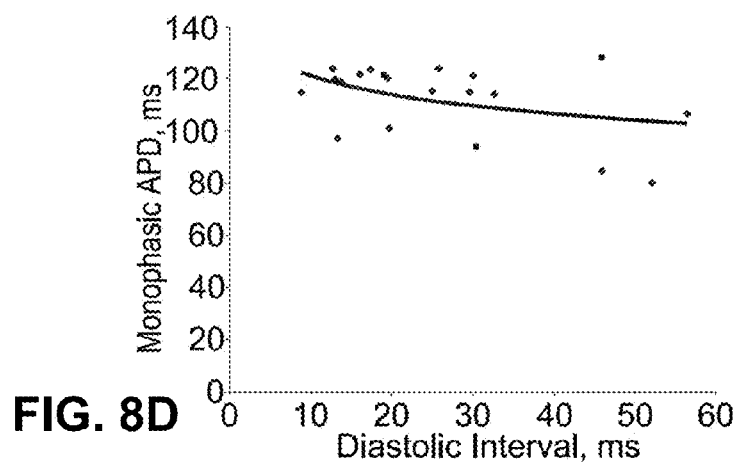
Figure 8E:
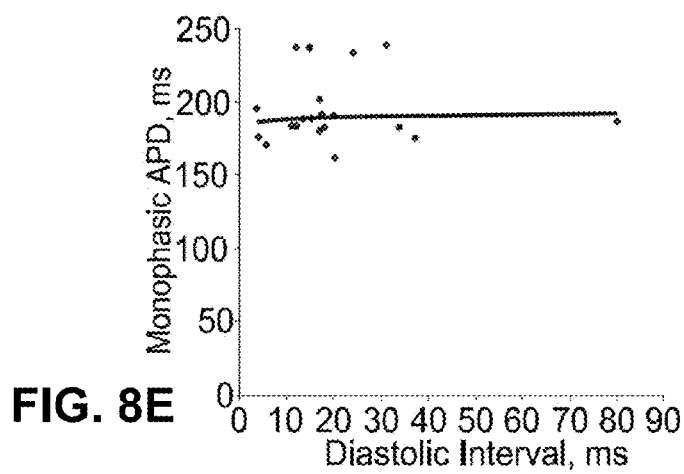

One approach embodied in the present invention is to create a 'hybrid' signal by inserting a physiological pattern at the time of each activation time onset (waveforms 660-670 in FIG. 7G). The physiological pattern may be obtained by averaging recorded signals over time (algebraically, from the median beat average or other method), averaging signals at neighboring locations (spatial averaging), from monophasic action potentials at various locations (waveforms 660-670), by filtering existing unipolar or bipolar signals in the frequency or time-frequency domain, or by using stored patterns from a database FIG. 1, database 160). When stored signals are used, properties including duration of these physiological patterns may be adjusted for rate using rate-response (restitution) behavior. Stored signals may be obtained from this patient, another patient with similar characteristics or another stored relationship. These processes may be applied to individual activations, or to the entire signal.

This method results in a physiological representation of activity at each location over time that may otherwise be difficult to obtain in the beating heart of patients during minimally invasive procedures. It has applications outside of heart rhythm disorders. For instance, said physiological pattern may be a model of cellular ion function. This enables the function of these ion currents at each sensor to be modeled cells timed to each observed activation, for the study of dynamics of calcium fluxes, potassium currents or other processes within the beating heart of this patient. By way of a further example, this physiological pattern may be a model of a pharmacological ligand, allowing study on the behavior of the beating heart to specific pharmacologic agents. In the gastrointestinal tract, cellular hormone release models may be studied for each peristaltic "beat." In the brain, known kinetics of neurotransmitter or endorphin release for discrete brain waves (non-invasive, via the scalp electroencephalogram or invasive, as surgery) may help to understand and treat various conditions. Treatment of conditions of epilepsy, for example, using the present invention is one embodiment of the invention. This invention also includes a method for determining the effect of a pharmacological or bioeffecting agent on the body by correlating the behavior of the beating heart or rhythm of another body part with the release, binding capacity or rate, or other action of the agent on the body.

An activation trail is then determined from sequences of activation in the physiological signal at multiple locations. The simplest form of this analysis is to order activation at each location sequentially in time. In other embodiments, analysis may identify and locate causes for a rhythm disorder using frequency domain methods, time-domain methods or spatial-phase methods. Frequency domain methods include the Hilbert transform or wavelet transform or phase delay methods. Spatial phase methods involve analyzing the spatial inter-relationships between sites showing activation at a certain location, in order to define the activation trail.

Pertaining to phase-space methods, a well-known technique assigns a phase $\phi$ to the signal at every electrode and at every time point. The phase at the exact location of the tip of the rotor is undefined and summing up the phase of neighboring electrodes results in a "phase jump" of $2\pi$. Thus, a rotor location corresponds to a phase singularity. Mathematically, these phase singularities can be found by evaluating a line integral over a closed curve as $\oint \vec{\nabla}\phi \cdot d\vec{l} = \pm 2\pi$ where the line integral is taken over a path l surrounding the phase singularity. Since the signal from the electrode is a single observable, the determination of the phase requires special attention. We will employ several different methods depending on the quality of the electrode signal.

The first phase-space method will be utilized if the signal from the electrodes is noisy and/or has a small amplitude. In this case, activation times for each electrode will be determined, followed by a novel analysis of wave front dynamics. As a first step, the spatial resolution of the probes and their activation times may be increased using a bi-linear interpolation scheme that interpolates activation using a fine regular grid created across the surface. In high quality physiological signals that contain activation, recovery and diastolic interval information, this results in a time trace V(t) for each point of the refined grid.

Figure 9A:
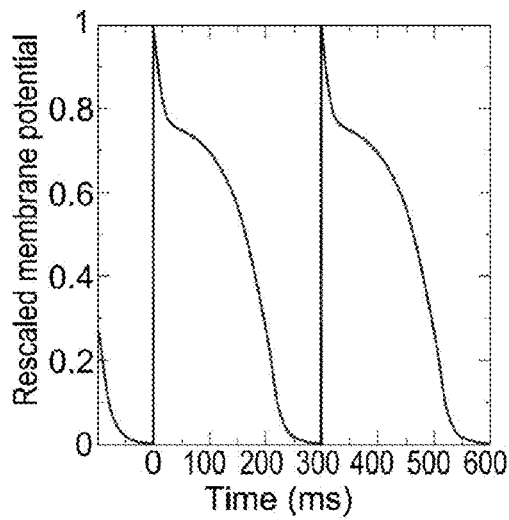
FIGS. 9A-9C show examples of direct assignment of phase.
Figure 9B:
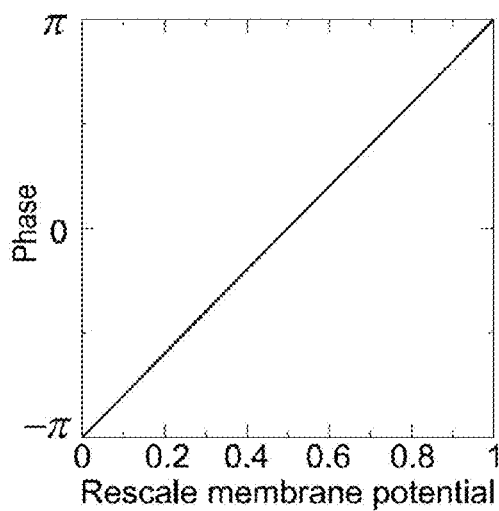
Figure 9C:
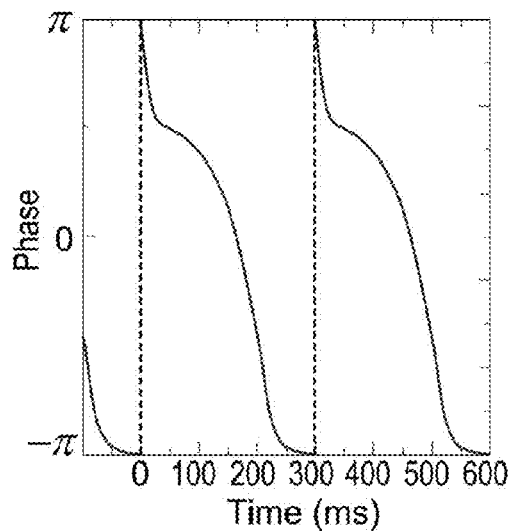

Since the shape of the action potential may be stable between beats, the method next defines a mapping from the membrane potential V to the phase $\phi$. This map assigns a unique value of $\phi$ to each value of V such that the maximum and minimum of the phase variable differs by $2\pi$. The detailed form of this map is arbitrary and the phase is computed using $\phi=2\pi(V-0.5)$. The corresponding time trace of the phase variable results in construction of the signal and its phase instantaneously as in FIGS. 9A-9C.

Once the phase map is constructed the method will calculate, for each time, the sum of the phase for all four points of the fine regular grid separated by a grid spacing that form a square (topological charge method). A result not equal to zero indicates the existence of a phase singularity and a rotor. The analysis will be further aided by the tracking of wave fronts. The location of these fronts will be computed using the regular fine grid by determining where and when V crosses a threshold value with a positive derivative dV/dt. Performing this calculation along the x and y direction of the fine regular grid and using linear interpolation between the grid points, will result in a set of points that lie on the wave front.

The wave front is then constructed by connecting these points. A similar analysis will be performed for phase, where isophase lines are tracked. A two-dimensional visual representation is then constructed that plots for each time point the value of the membrane potential using a grayscale or color scale, lines representing the wave fronts, lines representing similar phase (isophase lines), and symbols locating the phase singularities. This visual aid will greatly benefit the practitioner in interpreting the results of the inventive process and system. Note that the crossings of the lines representing the wave fronts and the isophase lines represent the phase singularity. Phase singularities indicate core regions, and thus can be used to localize the rotors.

The phase transform is able to demonstrate focal beats in AF—typically as centrifugal sources emanating from a localized area. A focal beat is characterized by a location that fulfills three criteria: 1) its activation time is earlier that at surrounding locations; 2) this region was previously inactive (in diastole) for a specified period of time; 3) the subsequent spread of activation emanates radially from the core region. Recognizing these 3 criteria, the invention finds these sources automatically. This algorithm will first determine locations that exhibit activation times ahead of their four nearest and four next-nearest neighbors and mark these as potential focal sources. Next, it determines the activation times at locations surrounding a potential focal source. If the activation times of these locations are earlier than their surrounding electrodes, the potential focal source is confirmed and is marked accordingly. These sites are plotted using our plotting technique as described above, greatly aiding the practitioner in localizing and interpreting these sources.

Alternatively, frequency domain methods may be used. On the physiological signal during the heart rhythm disorder, that may be the recorded signal or a signal derived after filtering, noise reduction and other strategies described above, one may employ several methods.

Figure 12C:
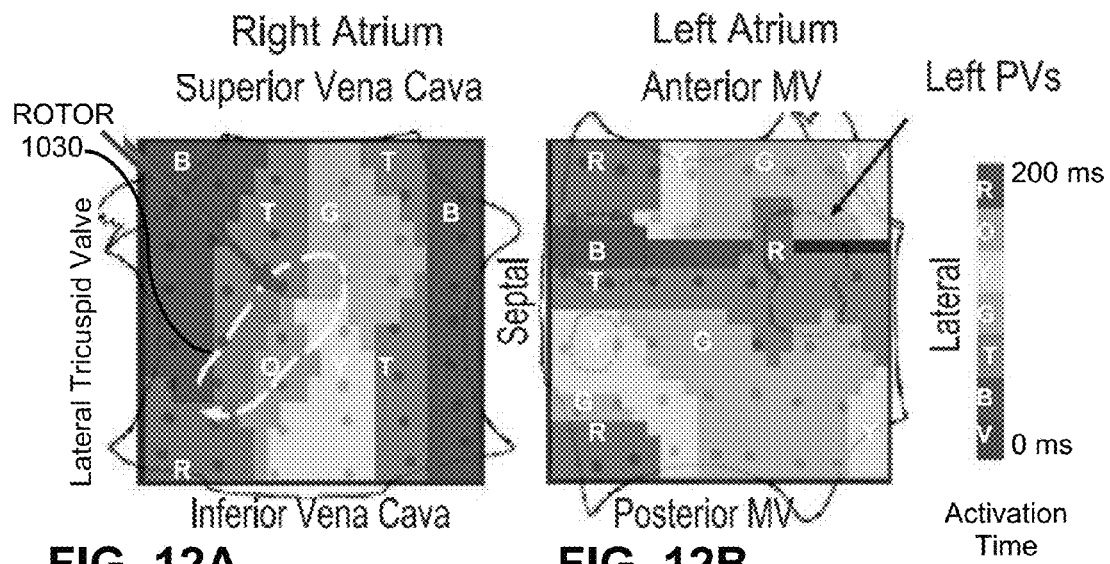
Figure 12C:
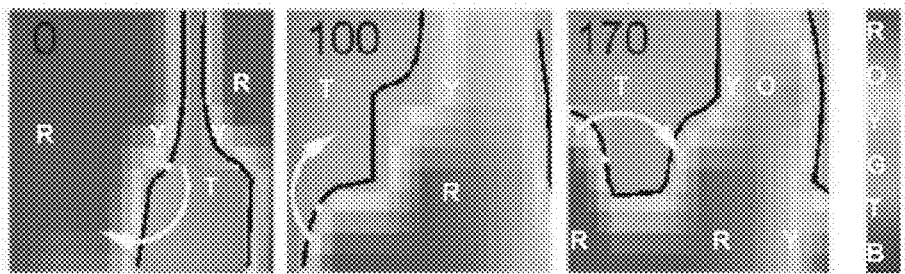

One such method is the Hilbert transform. The Hilbert transform shifts the phase of the negative frequencies of a signal by $\pi/2$ and the phase of the positive frequencies by $-\pi/2$. In this approach, determination of the phase $\phi$ of the signal is achieved by plotting voltage against the Hilbert transform of the voltage. The particularly useful embodiment applies a detrending algorithm to set the voltages at the activation times (maximum MAO to zero. The Hilbert transform is used to construct the phase plane of detrended signals. The Hilbert transform at all locations is interpolated across the fine regular grid created across the biological surface. Phase is then calculated from the state-space plot of voltage versus its Hilbert transform. Again, the spatial distributions of phase will be analyzed with the topological charge technique described above to locate phase singularities associated with phase singularities (the ends of wavefronts) such as at the tip of a reentrant wave. Activation wavefronts are constructed using the same technique as described above while isolines of zero phase will also be tracked. An example of our methods in the human atria is shown in FIGS. 12A and 12C, which show rotors in the left atrium computed using frequency-domain methods.

Another useful method employs a time delay embedding technique to determine the phase of the signal. This technique consists of plotting $V(t+\tau)-V^*$ vs. $V(t)-V^*$ for a fixed time delay $\tau$ and offset $V^*$, resulting in a value of the phase $\phi$ for each time point and each location. In practice, the time delay and offset will be determined by the practitioner after examining these plots for several locations using different values for r and $V^*$. Optimal values lead to trajectories that do not cross (that would lead to a non-unique value for the phase) and that encircle the origin (ensuring that the minimum and maximum phase differs by $2\pi$). Both the signal and the phase are interpolated across a fine regular grid created across the biological surface. The resulting phase map will then be examined for phase singularities and wave fronts will be tracked as described above.

Yet another useful method used to determine the phase of the signal is a wavelet transform. The exact form of this wavelet is variable, and an example includes the Haar wavelet. The wavelet transform will be computed for each location. The wavelet allows us to view the signal in multiple frequency resolutions. This will enable us to filter unwanted noise at specific frequencies (or frequency bands). In this approach, the phase transformation is achieved by plotting voltage against the phase shifted wavelet transform of the voltage. Once the phase $\phi$ has been calculated, we will precede as before, including refining the grid through bi-linear interpolation, finding phase singularity and tracking wave fronts.

Other information, such as locations within the organ of sites of rapid rate during the rhythm disorder, the presence of very regular sites surrounded by less regular sites, the presence of stable beat-to-beat configuration (shape) for successive signals as opposed to varying signal configurations, proximity to anatomic features known to be associated with particular rhythm disorders (such as pulmonary veins in AF, His-Purkinje system in VF), or a combination thereof may also assist in identifying and locating sources.

Several types of activation trails may result, producing corresponding discernible signature patterns for various types of causes for a rhythm disorder. An activation trail in which sequences of activation revolve around a central "core" region is termed a rotor. An activation trail that emanates radially from a core region is termed a focal beat (or a site of repetitive focal activations or beats). Another activation trail type is a dispersed pattern, in which a localized source is not clearly identified. In particularly useful embodiment, in such cases, signal sensing is repeated at additional locations or for additional periods of time. Localization of a cause for a heart rhythm disorder is based on the location of the core region and additional activation from this region. Some embodiments identify the core region directly. For instance, the Hilbert Transform and direct phase assignment methods identify the core region as the site where real and imaginary parts of the analysis intersect. In contrast, the direct sequential ordering method of the present invention indicates a core region either visually or analytically.

Figure 10:
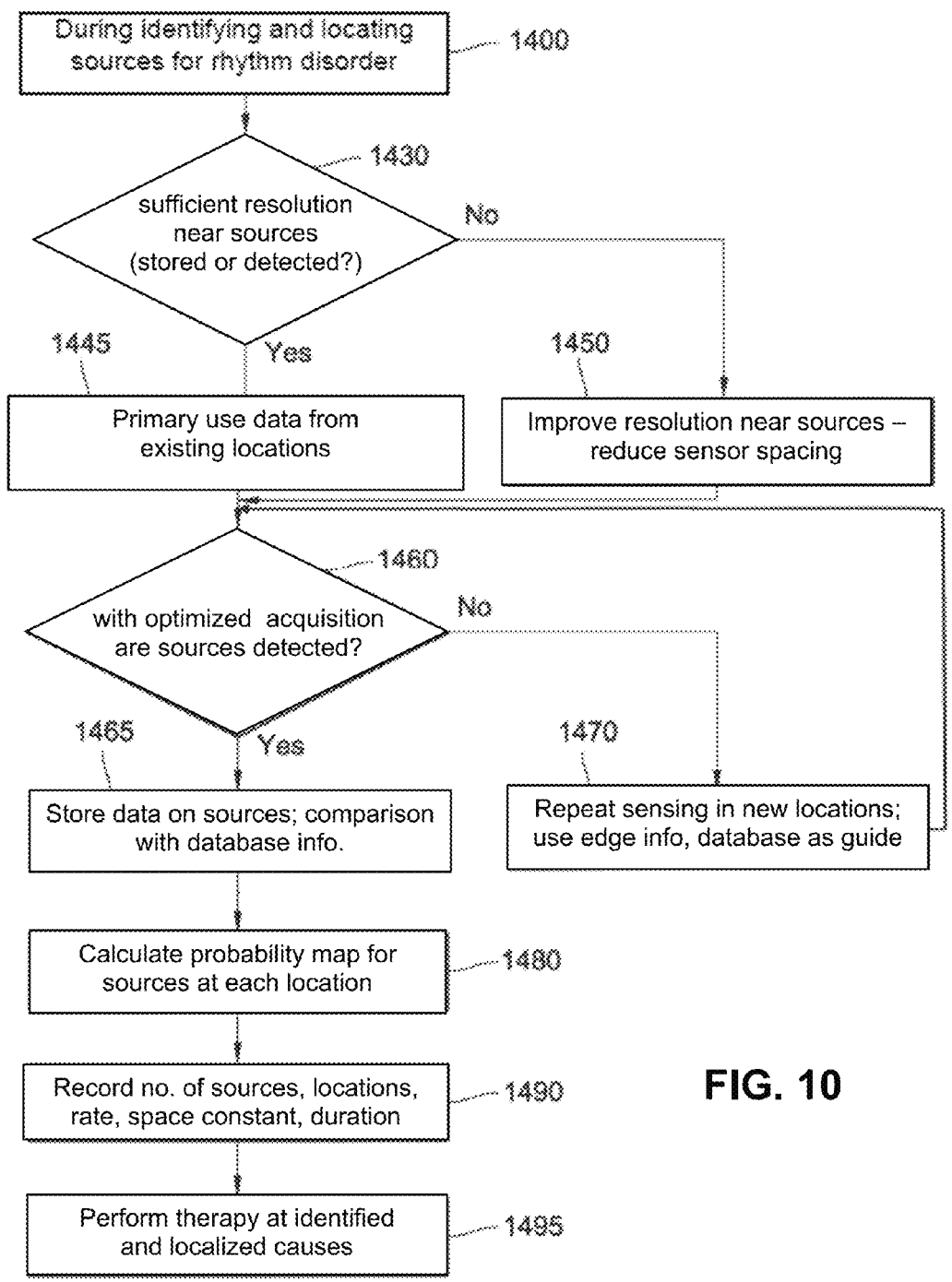
FIG. 10 is a flowchart of an embodiment, showing how sensed signals and stored data in a database can be used to create and use a probability map to improve clarity for identifying and localizing causes for a biological rhythm disorder.

In FIG. 10, operations 1400-1495 describe the process of identifying, locating and selecting cause(s) that are most likely to indicate primary causes of the rhythm disorder. In one particularly desirable embodiment, a probability map 1480 for sources of the rhythm disorder is constructed. This indicates likelihood that each sensed location harbors a cause of the rhythm disorder, relative to other sensed locations. A higher relative likelihood is assigned for sites where core regions sustain for longer periods of time (or, for more rotations or beats), where the rate of activation is faster, where the rate of activation is more organized, that activate surrounding tissue in a 1:1 fashion (thus, there is electrogram linking) and activate larger regions of tissue in phase (and thus have a large space constant), when fewer concurrent sources are identified, for sources that lie near known regions of high likelihood for rhythm disorders such as the pulmonary veins in human AF, for sources with less migration over time, and for rotor versus focal beat types of source. In one particularly useful embodiment, probabilities are assigned after comparison with stored examples in a database; the comparison may take the form of a stepwise multivariate comparison. In the limited case, a spatially fixed source that is a solitary electrical rotor and that directly activates the entire organ is by definition a primary cause of that heart rhythm disorder.

Surrogates for the activation trail also exist. These are data that approximate the identification and localization provided by the invention using data from fewer locations, less lengthy or detailed recordings, or using information from other resources such as the ECG rather than from within the heart. Thus, surrogates enable approximation of the activation trail using a reduced number of sensor locations compared to an analysis that directly measures the activation trail. These surrogates, used independently or in combinations, include sites of rapid rate during the rhythm disorder, the presence of very regular sites surrounded by less regular sites, the presence of stable beat-to-beat configuration (shape) for successive signals as opposed to varying signal configurations, signals where amplitude is particularly low, signals that are very prolonged for each activation is very prolonged, proximity to anatomic features known to be associated with particular rhythm disorders (such as pulmonary veins in AF, His-Purkinje system in VF), or a combination thereof may also assist in identifying and locating sources.

Surrogates may be detected from the ECG, and thus be used to plan a procedure or guide therapy in a patient.

Vectorial analyses of the ECG for regions of regularity and high rate, particularly if surrounded by regions of lower regularity and rate, indicate locations within the heart where sources lie.

FIG. 10, operations 1400-1495, summarize the approach to identify and locate sources. Operations 1400-1450 determine if sufficient sensor resolution is present to identify a cause. Criteria for sufficiency include the absence of discontinuities in the wave front calculation, and absence of jumps in the location of core regions, and an absolute sensor spacing that should not exceed approximately 1 cm. This is based upon computations that the minimum circumference of a reentry wave is >2 cm in the human atrium and larger in the human ventricle. Operations 1460-1490 then use a combination of optimized sensed data and stored data to compute sources, that are then treated, operation 1495. The present invention includes the wide use of filtered or unfiltered clinical data, data from a database including this and other patients, or computational estimates to represent the signal to be analyzed as well as the results of analysis. In addition, the hybrid use of existing patient-acquired data, signal processing methods, numerical methods and stored signals from a database are major advantages of the inventive process and system, particularly because high-resolution physiological data from human atria or ventricles may be extremely difficult, if not impossible, to obtain at clinical electrophysiologic study without open heart surgery.

All of the above approaches may be applied to any complex rhythm, including VF. Of course, these approaches may also be applied to "simple rhythms" such as reentry around an anatomical obstacle or rotors anchored at scar tissue (such as atrial flutter).

These inventive processes may be implemented in software, operated very quickly and are suitable for real-time, as well as off-line analysis, using small scale components such as those found in implantable devices, portable ambulatory machines, wristwatch-sized devices, as well as larger scale computers found in electrophysiology laboratories.

Mode 3. Storing Data on Heart Rhythm Sources in Database

Data on sources for rhythm disorders desirably may be stored in a database 160. This may be useful to classify sources in different patients, to help identify sources in a single patient, or to determine if a patient has returned with the same or a different source. Data in the database will thus include the characteristics described above, including the number of concurrent sources, rate, variability in rate over time, duration, size of biological organ whose activation is directly caused by the source (the space constant), location, whether this location migrates over time, rate within multiple regions of the heart at the time that the source was detected (such as left and right atrial rate during AF), and the response of each source to ablation.

Additional information to be stored in the database include one or more clinical factors from a group comprising gender (male/female), age, weight, height, presence of diabetes mellitus, blood pressure, atrial size, ventricular size, regions of atrial or ventricular scar, the left ventricular ejection fraction.

In a particularly useful embodiment, the database of AF Sources 160 will be continuously updated, based upon new source localization from additional cases. This will be used to help source localization for practitioners studying new patients, by way of a software expert system that will match the new patient to already stored patterns.

Source data to be stored will be analyzed for consistency with existing data, matched by the above variables. Only raw data that meets rigorous standards for data integrity will be incorporated, others will be rejected. After ensuring data integrity, data will be added to the database to improve localization for future patients.

The invention and database interface may include an expert system that compares current data with stored data. Based on the closest match or matches, logic within the invention determines if additional heart rhythm sources or additional characteristic should be studied, and whether they may lie based on stored information. This uses a "goodness of fit" against various stored parameters. This functionality is included because in practice, the number of sensed locations is limited by time constraints, in practice, many sensor locations may provide suboptimal data, thus limiting the actual sensed resolution, and because the inventor has observed that many patients show similar source locations and characteristics.

Database updates will be available to the practitioner regularly from a centrally located, secured database that contains the above information. No information on patient name, geographical location, study date or other items prohibited by the Health Information Portability Act (HIPAA) will be included. This database will be maintained at a remote location but available electronically by means including wired and wireless communication, electronic media such as CDs, DVDs, and solid state storage devices.

Mode 4. Display of Sources of Biological Rhythm Disorder

The invention includes methods and apparatus to communicate the identification, location and above characteristics of sources for biological rhythm disorders to the practitioner. This includes a visual display means, typically in the form of a graphical display on a computer monitor, or a printout showing the source in relation to cardiac anatomy, or a basic textual line summary of the location and/or sensor site where the source lies.

An auditory display may also be used, that vocalizes the identification, location and above characteristics of sources for biological rhythm disorders to the practitioner. In one embodiment, this would include the conclusions or a summary of analysis rather than the analysis results themselves.

Mode 5. Therapy at Causes of Biological Rhythm Disorder

In addition to the processes and systems of the invention used to detect and diagnose the cause of the rhythm disorder, the invention also includes devices and methods to treat the source for the biological rhythm disorder, in order to modify, ameliorate or eliminate said rhythm disorder.

Treatment of the source may employ any useful technique, including ablation with radiofrequency, freezing energy, microwaves or other sources. Modification may also include cell therapy (such as with stem cells), gene therapy, pharmaceutical delivery, ionizing or non-ionizing radiation delivered by devices inside or outside the heart, or other interventions.

Treatment is delivered to modify the cause. In a simple heart rhythm disorder such as atrial tachycardia or atrial flutter, energy is applied directly to eliminate the cause. In a complex rhythm disorder, such as AF, energy can be applied to ablate (destroy) the source, to isolate the source by destroying tissue between the source and the remainder of the viable heart chamber, or to modulate the interaction between different sources. This latter form of treatment is very novel and has been shown in experiments by the inventor to be extremely effective. Modulation may be performed in a stochastic fashion.

In a particularly desirable embodiment, therapy is targeted at the core region of an identified or localized cause for the rhythm disorder, with the intention of eliminating this cause to treat the heart rhythm disorder. This may be applied sequentially to identify, locate and treat more than one cause for said disorder.

Alternatively, therapy may be targeted at locations neighboring the core region for a source, with the intention of disconnecting the source from surrounding tissue.

Alternatively, therapy may be targeted at locations neighboring the core region for a source, with the intention of causing the source to migrate towards tissue where definitive treatment is more easily accomplished. For instance, if the source lies at a location where ablation is difficult due to anatomy, tissue thickness or other factors, ablation on one side of the source may cause it to migrate towards a location that is easier to ablate due to thinner tissue or anatomic factors.

Alternatively, therapy may be targeted at locations neighboring the core region for a source, with the intention of preventing movement of the source and thus compartmentalizing it.

Alternatively, therapy may be targeted at locations neighboring the core region for a source, with the intention of reducing the mass of tissue available for the source to sustain and thus causing it to terminate.

Treatment may take the form of ablation, delivered via a catheter in the heart (element 25 in FIG. 1), on the epicardial surface, or an electrode present on one of the multi-electrode catheter designs included herein, for example see FIGS. 2-4.

When a dispersed activation trail is observed, locations where sources may lie that are difficult to identify are targeted first. In patients with AF, such sites include the pulmonary veins and other thoracic veins, and the atrial appendages. Thus, pulmonary vein isolation is performed first, followed by therapy at additional sites if clinically suspected. Signal sensing is then repeated to identify and locate a cause.

In preferred particularly desirable embodiment, the multi sensor catheter (FIGS. 2-4) includes an assembly that can deliver therapy in the form of ablation. In this embodiment, sensors at locations where the source lies are activated to deliver ablation energy to modify or eliminate the source.

The system may deliver therapy in a spatial locus, as well as at fixed locations. In this system, the location of the source core region is analyzed constantly throughout therapy. Therapy, such as ablation energy, is directed at varying locations and potentially multiple locations to constrain movement of the source. An analogy is to construct a "fence" of ablated tissue around a moving source in order to keep it in one location. This may require therapy delivery (such as ablation) at multiple sensors of said poles of said assembly concurrently. This process is continued until the rhythm terminates or a remote source becomes dominant.

This invention is well suited to target therapy performed surgically in the operating room with direct exposure of the heart. This may be via a minimally invasive approach or traditional open chest heart exposure. The choice of recording electrode, sock, plaque or other equipment is up to the discretion of the surgeon and does not alter the principles of therapy.

Alternatively, said modulation can be applied by stimulating (pacing) the tissue. For pacing, the process controller 70 conditions the pacing module 50, to stimulate the heart using electrodes 20, 21, 22, 23 and 25 in the heart, electrodes 30 on the body surface, or electrodes elsewhere, such as electrode 150 in the esophagus. The electrode controller 40 receives signals from the electrodes before, during and after pacing. Pacing is used to increase heart rate and introduce extra beats.

In alternative embodiment, the invention can ablate or stimulate cardiac nerves to modify or eliminate the source. Thus, if sources lie at locations of heart ganglionic plexuses, ablation or pacing of such locations can be used to modify the source.

If the abnormal rhythm terminates after modify or eliminating sources, attempts can be made to restart the rhythm. In the case of heart rhythm disorders, this may include very rapid pacing, the administration of isoproterenol or other interventions. The entire application of this invention is then repeated.

In the event that the abnormal rhythm can no longer be initiated, the physician may exercise the discretion to modify additional regions that may be potential sources. This information may be available directly from stored data in the database, matching patients with a similar classification to the current patient.

Mode 6. Non-Real-Time Review Mode

In an important mode of operation, the invention can be used in a non-real time, offline analysis fashion. This review mode can be applied to data from this individual at another time, such as a prior electrophysiologic study, data from a different device (such as an implanted pacemaker or defibrillator) or even a prior failed ablation. This can be used to review results from a prior procedure, to review data from a patient prior to planning the application of this invention, or to assess if the same patient now presents with the same or a different source for their rhythm disorder.

Signals are first uploaded from stored electrograms in a database 160 to the processor controller 70. This database can be the master database that stores data on multiple patients, or a patient-specific database. Data storage and retrieval can be implemented for any signal type. Stored signals can be derived from another source, a catalogued source, or computed or virtual signals such as from ENSITE 3000® or ENSITE NAVX® by St Jude Medical, or CARTO® by Biosense-Webster. Signals may also be derived from a different individual, querying the database for a patient with similar demographics and heart rhythm disorder.

In a separate non-real-time mode, data obtained when the patient is not in the heart rhythm disorder can be used by the invention to identify and locate sources for a rhythm disorder. This may be useful, for example, if the heart rhythm disorder is not observed at the time of a procedure, and cannot be started using conventional methods. This mode uses biological properties of the chamber to predict locations where sources/causes may lie when in the heart rhythm disorder. Such locations include sites where the maximum slope of action potential duration restitution is >1, sites where beat-to-beat oscillations in the repolarization signal shape or duration are observed, or where conduction velocity restitution is broad to indicate slowed conduction at critical rates.

In the preferred embodiment, to measure restitution it is necessary to sense signals for a wide range of rates at each location, as indicated in FIG. 1 element 90. This may be achieved using pacing. In this case, the process controller (FIG. 1, element 70) conditions the Pacing module 50, to stimulate the heart using electrodes in the heart 20-25, on the body surface 30, in the esophagus 150 or elsewhere. The wider the range of rates, particularly fast rates, the more comprehensive the data range for that signal for analysis of restitution. When pacing is not an option, the invention will prompt the user to increase heart rate using other options or to use stored information from a database.

In this embodiment, the rate-response ("restitution") curve is created at each rate for each component of signals shown in FIG. 5. For example, this step may compute how monophasic action potential duration (time from phase 0 to phase 3) varies with rate (APD rate restitution). Examples of atrial APD restitution are shown in FIGS. 7A-7G and 8A-8E. Using pacing to increase the range of sampled heart rates provides a comprehensive assessment of rate response of each biosignal.

FIGS. 7A, 7C and 7E illustrate a useful embodiment whereby of human action potentials recorded in the left atrium 420 provide high quality information including depolarization (phase 0), repolarization (phases 1-3), phase 2 amplitude and action potential duration (time interval from phase 0 to phase 3). Phase 4 indicates the interval between one beat and the next. The invention may determine rate response (restitution) of multiple components, focusing on rate-response of AP duration (time from phase 0-3), and AP phase II amplitude.

Reference 400 (FIG. 5) is an ECG. This includes intra-atrial components (the P wave and PR interval), and ventricular components including depolarization (the QRS complex) and repolarization (the T wave). For atrium, the invention records how P-wave duration varies with rate, using analyses shown later in FIGS. 7A-7F. For the ventricle, the invention records how QT interval varies with rate as a measure of ventricular APD rate-behavior (restitution). Individual QRS complexes are aligned using one of several columnar techniques, including methods that align electrograms about the point of largest positive or negative slope, their peak values or minimize their mean square differences, or metrics based on derived signals. T-waves are identified and aligned similarly. Atrial activity is considered to lie in the intervening intervals.

If the signal is a unipolar electrogram, it is also analyzed in analogous fashion. Each is analyzed for waveform shape as well as duration. FIG. 5, Items 430-440 indicate unipolar electrograms from the human left atrium 430 and left ventricle 440 respectively, with depolarization and repolarization measured collectively as the activation-recovery interval, a surrogate for the monophasic action potential duration. The invention determines adjustment of various components for rate.

Signals can also be bipolar electrograms (items 450, 460), and the invention determines rate response of each component.

In an alternative embodiment, ECG and electrogram data are uploaded from a database 160 for analysis in an analogous fashion to the described real-time mode of operation. Data from the database can be from the same or different patients, recorded at any time and using any acquisition system.

In AF, MAP restitution may differ from MAP when not in AF. FIG. 8 element 700 shows the initiation of AF after pacing. Element 710 shows MAP restitution during pacing in black. Immediately after AF onset (red points), APDs track previously derived MAP restitution. However, this may not be true for longer-lasting AF. Elements 720, 730 and 740 show patients with long-lasting AF, in whom APD restitution differs from that obtained in pacing prior to AF.

Thus, it may be advantageous to use APD restitution obtained from the patient in AF, at this time or a previous time, or from stored APDs in this or other patients, or filtered or computed data, for signal processing and analysis.

Locations where sources may arise during a subsequent heart rhythm disorder may now be predicted from these analyses. For monophasic action potentials, site where the maximum slope of MAPD rate-behavior (restitution)>1 may be immediately adjacent to causes for VF or AF. Other indexes of high likelihood for the initiation of heart rhythm disorders include broad rate-response (restitution) of conduction, since such sites of dynamic conduction slowing may indicate sites where heart rhythm causes lie.

The energy generator 60 may be activated to apply destructive energy (either radiofrequency, cryoablation or microwave radiation) via the ablation electrode 25. This electrode can be moved within the heart manually by an operator, that is the traditional approach, or remotely using robotic or computer assisted guidance.

The implementation of the system described herein may be based largely upon digital signal processing techniques. However, it should be appreciated that a person of ordinary skill in this technology area can easily adapt the digital techniques for analog signal processing.

Various features of the invention are set forth in the following claims.

While the invention has been described in connection with particularly desirable embodiments, it is not intended to limit the scope of the invention to the particular form set forth, but on the contrary, it is intended to cover such alternatives, modifications, and equivalents as may be included within the spirit and scope of the invention as defined by the appended claims.

EXAMPLES

Identification and Localization of Cause for AF in 47 Year Old Man

Figure 11:
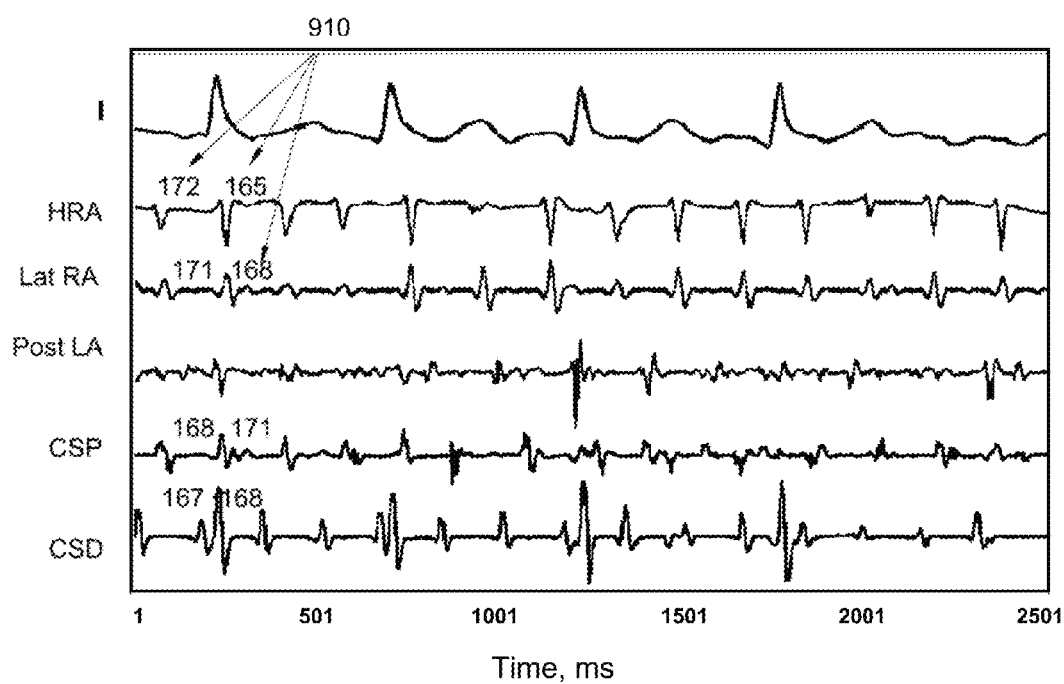
FIG. 11 is an example of use of the invention in a 47 year old man. Shown is a selection of signals (electrograms) from within the left and right atria and coronary sinus of a patient with atrial fibrillation presenting for therapy.

FIG. 11 illustrates pre-ablation signals for a representative patient, a 47 year old man with persistent atrial fibrillation (AF) for over five years. The patient continued to have symptomatic racing of the heart, which required him to visit hospital emergency rooms for treatment, despite various therapy with amiodarone and other appropriate therapy, and despite prior ablation procedures for AF. Given the severity of his symptoms, the patient therefore elected to return to the electrophysiology laboratory for further evaluation and ablation.

FIG. 11 shows signals from the right and left atria during AF at the commencement of electrophysiologic study. It can be seen that the AF cycle length (time between successive activation onset times) is quite short, shown as 172 ms and 165 ms for the first two cycles in the right atrium (arrows 910), and varies, as is typical for AF. Notably, signals were more fractionated and disorganized in shape in the left atrium (post LA') and coronary sinus ('CSP' proximal coronary sinus; 'CSD' distal coronary sinus) than in the right atrium ('HRA' high right atrium; 'Lat RA' lateral right atrium; 'post RA' posterior right atrium), as is common.

These findings would normally guide ablation towards the left atrium. A typical procedure in this case would commence by ablating near the pulmonary veins and confirming isolation, followed by additional ablation selecting at sites including: (a) left atrial sites of fractionated electrograms, linear ablation at the roof, linear ablation at the mitral annulus, other linear ablation, then (b) right atrial ablation including sites of fractionation and the cavotricuspid isthmus. This proposed procedure would take approximately 2-3 hours with a <50% chance of terminating AF, meaning that electrical cardioversion would be required to restore normal rhythm at the conclusion of the procedure (Calkins, Brugada et al. 2007).

Rather than use this known approach, an embodiment of the method and treatment of the present invention was applied. A catheter assembly containing 64 sensors (electrodes) was inserted via the femoral veins into the right atrium, and across a trans-septal puncture into the left atrium of the patient. These were connected via wire cables to a recording system for collecting signals at each sensor during AF. These signals were converted to digital form, and input into a computer program. Activation onset times were recorded for 2 seconds of AF at each sensor. While two seconds was used with this patient, any greater or lesser periods of time may be useful. Desirably, one second or less may be used. In some embodiments, milliseconds may be used. Activation onset times at each sensor location were sequentially ordered in time. Stored action potential tracings were used to create an electrograph (voltage-time series), by inserting said tracings at the activation time onsets for each sensor. Finally, a direct phase assignment technique was used to identify a core region. An activation trail is directly indicated by the relationship of these activation sequences to a core region—if they revolve around a core, then an electrical rotor is detected and considered to be a cause, but if they emanate radially from a core region, then a focal beat is detected and considered a cause. Results were displayed as an animation on a computer monitor for physician review.

The activation trail 1030 in FIG. 12A revealed an electrical rotor as the cause for this man's AF. In FIG. 12A, activation onset times can be seen to revolve around a core region in the right atrium at times color-coded from 10 ms (blue ("B")) to 200 ms (red ("R")). No localized cause was found in the left atrium, shown in FIG. 12B. FIG. 12C displays this same rotor in a different form, as three snapshots in time of tissue that is depolarized (activated; red ("R")) and repolarized (not activated, light blue ("LB")). Viewed chronologically (0 ms, 100 ms and 170 ms, from left to right), these snapshots also trace activation sequences revolving around a core region (a rotor). This core region had a high likelihood of being a cause, since it was a solitary source that controlled electrical activation for almost all of the surrounding atrium (large space constant).

Clinically, it was surprising that this electrical rotor lay in the right atrium. The right atrial rotor site neither showed high spectral dominant frequency, nor low amplitude fractionated signals, and would not normally be identified or targeted for ablation.

Figure 12D:
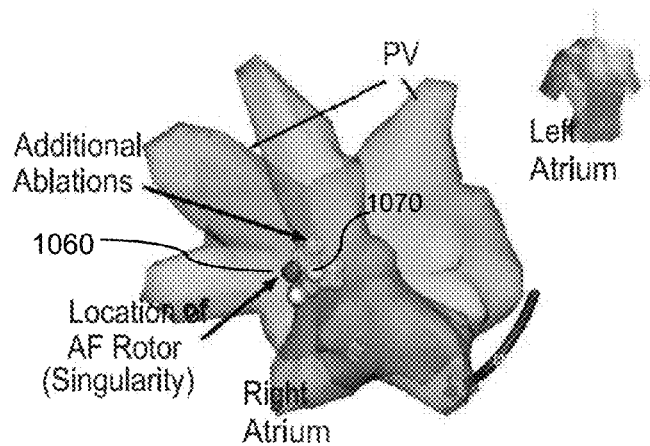
In FIG. 12D, the core region is shown in the lateral wall of the right atrium.
Figure 13:
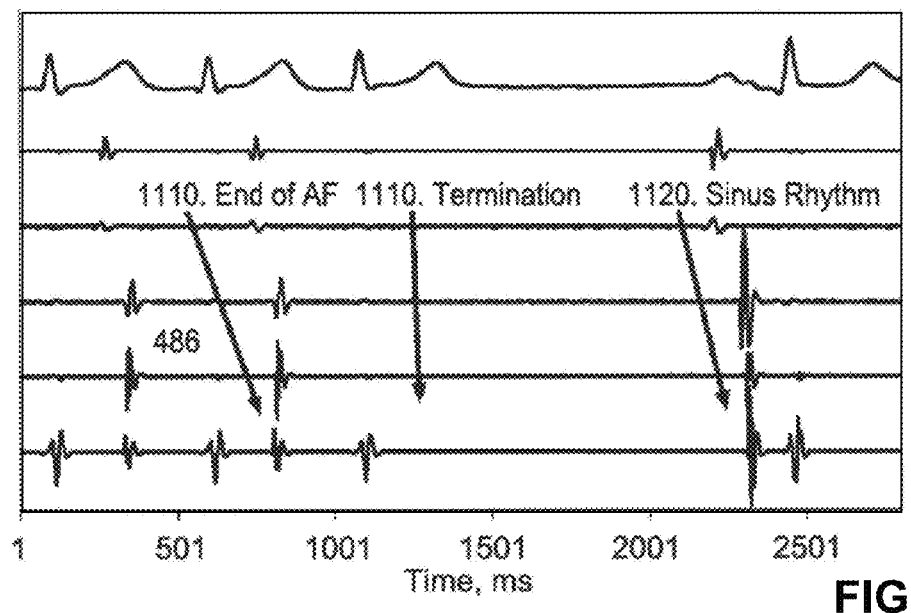
FIG. 13 shows that, during direct ablation at the core region identified in FIG. 12 for less than 6 minutes, the AF slowed and terminated to normal rhythm (sinus rhythm), thus demonstrating that the cause of the AF had in fact been located and successfully treated.
Figure 14:
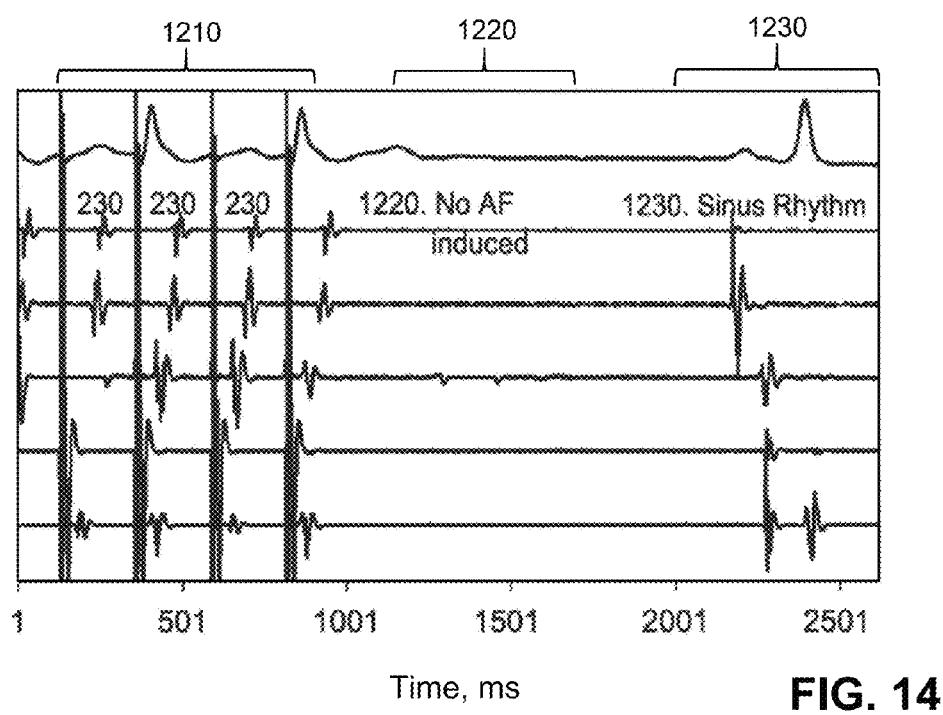
FIG. 14 shows that, after the AF had been terminated, it was not possible to restart the AF even by pacing the atria very rapidly (cycle length 230 ms, equivalent to over 260 beats/min). Faster rate pacing was now blocked (did not stimulate the atrium).

Ablation commenced directly at the rotor core in the right atrium, at a site indicated by the red (dark) dot 1060 in FIG. 12D. Notably, AF slowed within 30 seconds of energy delivery to a cycle length of 227 ms. Subsequent ablation at immediately adjacent sites, indicated by white dots 1070 in FIG. 12D, further slowed AF until it terminated to sinus rhythm within 6 minutes after ablation, as shown in FIG. 13. In FIG. 13, panels 1100 to 1120, AF can be seen to stop (arrow 1110), followed by the restoration of normal sinus rhythm (arrow 1120). At this point, AF could not be restarted using the typical technique of rapid pacing as shown in FIG. 14, where segment 1210 shows rapid pacing with capture of the atrium, segment 1220 shows no induction of AF, and segment 1230 shows sinus rhythm after the end of pacing.

This result is paradigm-shifting compared to the current state-of-the-art, where slowing of AF typically occurs after lengthy ablation that is widely and empirically applied (to 30-40% of the atrium), yet termination of persistent AF is still uncommon. Conversely, we acutely slowed and acutely terminated AF with ablation of less than approximately 2-3% of the atrium. Ablating only at one site identified a priori in persistent AF, and seeing immediate slowing and termination of AF is not known to have been performed previously.

Other Examples of Identification and Localization of Causes for AF

Figure 15A:
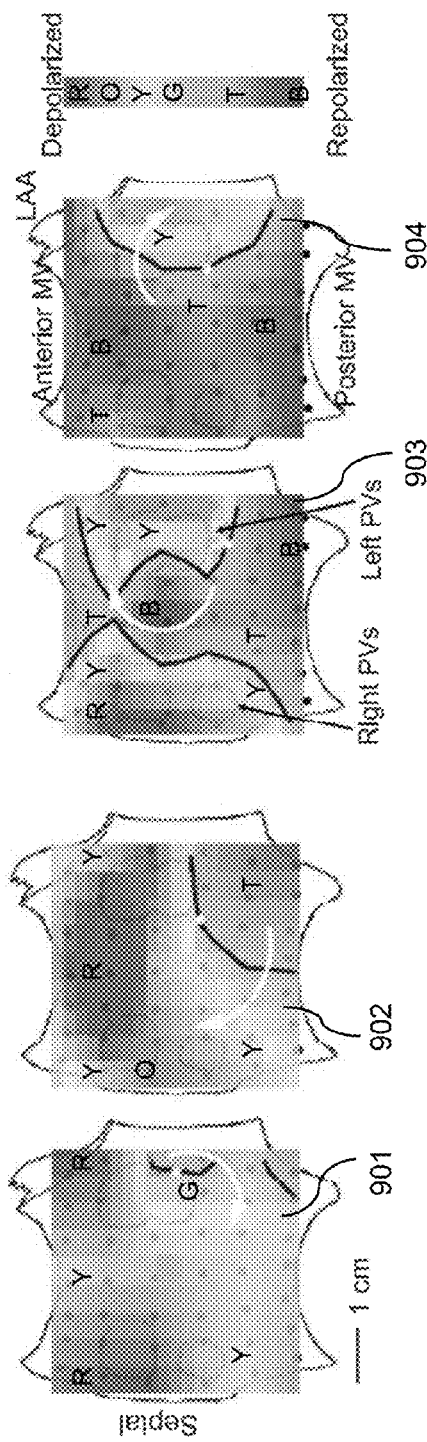
FIGS. 15A and 15B show patient examples of localized causes of human AF detected with this invention. Electrical rotors are shown in two patients in the left atrium.

A 77 year old man presented for ablation of atrial fibrillation (AF). His history was notable for paroxysmal AF despite multiple antiarrhythmic medications, a slightly enlarged left atrium (diameter 45 mm) and normal left ventricular ejection fraction (58%). At invasive electrophysiology study, catheters were inserted into the atria as described. The invention was applied to multiple sensors. FIG. 15A shows a localized source in the form of an electrical rotor near the left inferior pulmonary vein. Inspection of panels 901-904 from left to right (forwards in time) shows that the depolarized (activated) tissue in warmer colors (red ("R")) revolves clockwise around a core region on the medial lip of the left inferior pulmonary vein (see outline as black hourglass). Ablation at this site terminated AF acutely.

Figure 15B:
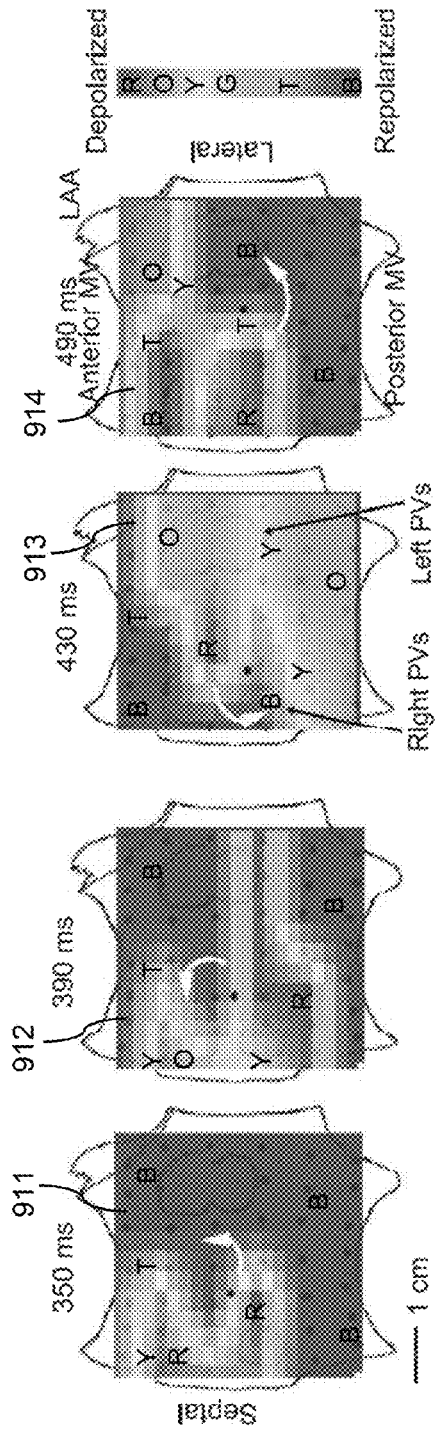

A 40 year old patient with persistent AF presented for ablation. The AF was resistant to flecainide and other anti-arrhythmic medications, his left atrial diameter was 52 mm and left ventricular ejection fraction was 69%. At invasive electrophysiology study, catheters were inserted into the atria as described above. The invention was applied to multiple sensors. FIG. 15B, panels 911-914 show a localized source in the form of an electrical rotor in the posterior wall of the left atrium. Again, viewing panels 911-914 from left to right shows that activated (depolarized) tissue revolves counter-clockwise around a core region on the posterior wall of the left atrium between the pulmonary veins. After ablation at this site, the patient remains free of AF.

Figure 16A:
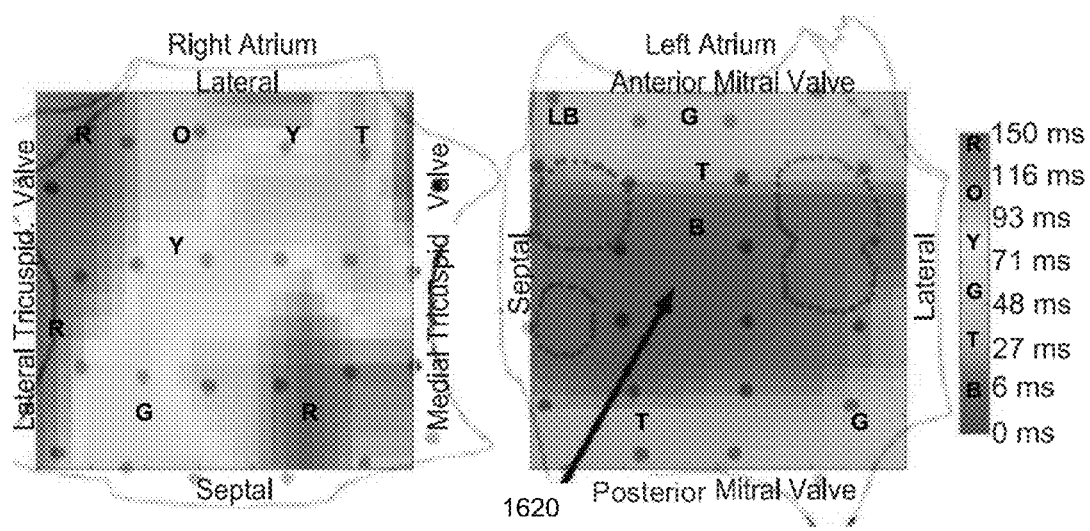
FIG. 16A shows an example of a localized focal beat cause of AF (1620) in the left atrium a 56 year old patient.
Figure 16B:
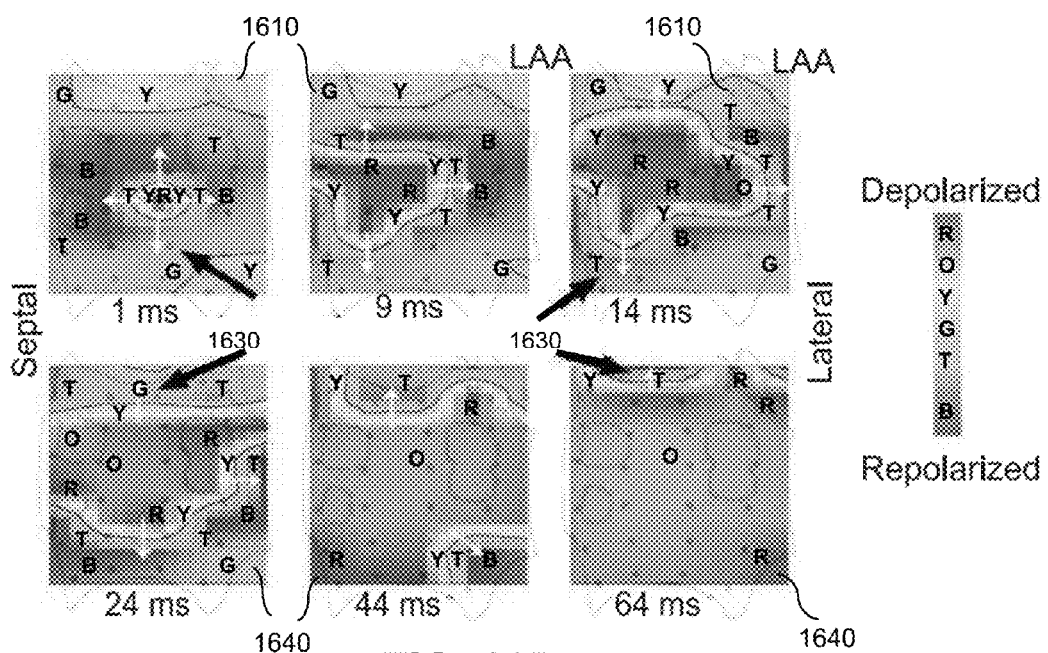
FIG. 16B shows the activation trail with activation emanating radially therefrom.

A 56 year old patient with paroxysmal AF and significant symptoms presented for ablation. The AF continued despite several anti-arrhythmic medications. His left atrium was moderately enlarged. At invasive electrophysiology study, catheters were inserted into the atria as described above. The invention was applied to multiple sensors. Panels 1610 of FIG. 16B show the output of a localized source in the left atrium, between the pulmonary veins although not lying at these veins. The source was repetitive, as indicated by arrow 1620 in FIG. 16A. The activation trail (indicated by arrows 1630) shows activation emanating radially from this site. In panels 1640 of FIG. 16B, left atrial activation is seen to be fibrillatory (disorganized). Ablation was applied to this focal beat cause, and AF terminated acutely. At the time of filing, the patient has been completely free from AF for several months. This is a paradigm shifting because normal ablation lesions in this patient, that circle the pulmonary veins, would have missed this source. Thus, this patient would likely have been one who would have recurred after ablation, if the prior art known techniques of treating AF had been used.

REFERENCES

Abreu Filho, C. A. C., L. A. F. Lisboa, et al. (2005). "Effectiveness of the Maze Procedure Using Cooled-Tip Radiofrequency Ablation in Patients with Permanent Atrial Fibrillation and Rheumatic Mitral Valve Disease." Circulation 112(9_suppl): I-20-25.

Allessie, M. A., J. Ausma, et al. (2002). "Electrical, Contractile and Structural Remodeling during Atrial Fibrillation." *Cardiovasc Res* 54(2): 230-246.

Bardy, G. H., K. L. Lee, et al. (2005). "Amiodarone or an Implantable Cardioverter-Defibrillator for Congestive Heart Failure." *N Engl J Med* 352(3): 225-237.

Calkins, H., J. Brugada, et al. (2007). "HRS/EHRA/ECAS expert Consensus Statement on catheter and surgical ablation of atrial fibrillation: recommendations for personnel, policy, procedures and follow-up. A report of the Heart Rhythm Society (HRS) Task Force on catheter and surgical ablation of atrial fibrillation. European Heart Rhythm Association (EHRA); European Cardiac Arrhythmia Society (ECAS); American College of Cardiology (ACC); American Heart Association (AHA); Society of Thoracic Surgeons (STS)." *Heart Rhythm* 4(6): 816-61.

Cappato, R., H. Calkins, et al. (2005). "Worldwide Survey on the Methods, Efficacy, and Safety of Catheter Ablation for Human Atrial Fibrillation." *Circulation* 111(9): 1100-1105.

Cappato, R., H. Calkins, et al. (2009). "Prevalence and causes of fatal outcome in catheter ablation of atrial fibrillation." *J Am Coil Cardiol* 53(19): 1798-803.

Cheema, A., C. R. Vasamreddy, et al. (2006). "Long-term single procedure efficacy of catheter ablation of atrial fibrillation" *J Interv Card Electrophysiol* 15(3): 145-155.

Cox, J. L. (2004). "Cardiac Surgery for Arrhythmias." *J. Cardiovasc Electrophysiol.* 15: 250-262.

Cox, J. L. (2005). "The central controversy surrounding the interventional-surgical treatment of atrial fibrillation." *J. Thorac. Cardiovasc. Surg.* 129(1): 1-4.

Ellis, E. R., S. D. Culler, et al. (2009). "Trends in utilization and complications of catheter ablation for atrial fibrillation in Medicare beneficiaries." Heart Rhythm 6(9): 1267-73.

Gaspo, R., R. F. Bosch, et al. (1997). "Functional Mechanisms Underlying Tachycardia-Induced Sustained Atrial Fibrillation in a Chronic Dog Model." *Circulation* 96(11): 4027-4035.

Kalifa, J., K. Tanaka, et al. (2006). "Mechanisms of Wave Fractionation at Boundaries of High-Frequency Excitation in the Posterior Left Atrium of the Isolated Sheep Heart During Atrial Fibrillation." *Circulation* 113(5): 626-633.

Knecht, S., F. Sacher, et al. (2009). "Long Term Follow-Up of Idiopathic Ventricular Fibrillation Ablation: A Multicenter Study." *J Am Coil Cardiol* 54(6): 552-528.

Masse. S., E. Downar, et al. (2007). "Ventricular fibrillation in myopathic human hearts: mechanistic insights from in vivo global endocardial and epicardial mapping." *Am J Physiol Heart Circ Physiol* 292(6): H2589-97.

Myerburg, R. J. and A. Castellanos (2006). "Emerging paradigms of the epidemiology and demographics of sudden cardiac arrest." *Heart Rhythm* 3(2): 235-239.

Nademanee, K. J. McKenzie, et al. (2004a). "A new approach for catheter ablation of atrial fibrillation: mapping of the electrophysiologic substrate." *J. Am. Coll. Cardiol.* 43(11): 2044-2053.

Narayan, S. M., D. E. Krummen, et al. (2006d). "Evaluating Fluctuations in Human Atrial Fibrillatory Cycle Length Using Monophasic Action Potentials." *Pacing Clin Electrophysiol* 29(11): 1209-1218.

Nash, M. P., A. Mourad, et al. (2006). "Evidence for Multiple Mechanisms in Human Ventricular Fibrillation" *Circulation* 114: 536-542.

Ng, J., A. H. Kadish, et al. (2006). "Effect of electrogram characteristics on the relationship of dominant frequency to atrial activation rate in atrial fibrillation." *Heart Rhythm* 3(11): 1295-1305.

Ng, J., A. H. Kadish, et al. (2007). "Technical considerations for dominant frequency analysis." *J Cardiovasc Electrophysiol* 18(7): 757-64.

Oral, H., A. Chugh, et al. (2007). "Radiofrequency catheter ablation of chronic atrial fibrillation guided by complex electrograms." *Circulation* 115(20): 2606-12.

Oral. H., A. Chugh, et al. (2009). "A randomized assessment of the incremental role of ablation of complex fractionated atrial electrograms after antral pulmonary vein isolation for long-lasting persistent atrial fibrillation." *J Am Coll Cardiol* 53(9): 782-9.

Reddy, V. Y., M. R. Reynolds, et al. (2007). "Prophylactic catheter ablation for the prevention of defibrillator therapy." *N Engl J Med* 357(26): 2657-65.

Ryu, K., S. C. Shroff, et al. (2005). "Mapping of Atrial Activation During Sustained Atrial Fibrillation in Dogs with Rapid Ventricular Pacing Induced Heart Failure: Evidence for a Role of Driver Regions." *Journal of Cardiovascular Electrophysiology* 16(12): 1348-1358.

Sahadevan, J., K. Ryu, et al. (2004). "Epicardial Mapping of Chronic Atrial Fibrillation in Patients: Preliminary Observations." *Circulation* 110(21): 3293-3299.

Sanders, P., O. Berenfeld, et al. (2005a). "Spectral Analysis Identifies Sites of High-Frequency Activity Maintaining Atrial Fibrillation in Humans." *Circulation* 112(6): 789-797.

Singh, B. N., S. N. Singh, et al. (2005). "Amiodarone versus Sotalol for Atrial Fibrillation." *N Engl J Med* 352(18): 1861-1872.

Skanes, A. C., R. Mandapati, et al. (1998). "Spatiotemporal Periodicity During Atrial Fibrillation in the Isolated Sheep Heart." *Circulation* 98(12): 1236-1248.

Tabereaux, P. B., G. P. Walcott, et al. (2007). "Activation patterns of Purkinje fibers during long-duration ventricular fibrillation in an isolated canine heart model." *Circulation* 116(10): 1113-9.

Vaquero, M., D. Calvo, et al. (2008). "Cardiac fibrillation: From ion channels to rotors in the human heart." Heart Rhythm.

Waldo, A. L. and G. K. Feld (2008). "Inter-relationships of atrial fibrillation and atrial flutter mechanisms and clinical implications." J Am Coil Cardiol 51(8): 779-86.

Warren, M., P. K. Guha, et al. (2003). "Blockade of the inward rectifying potassium current terminates ventricular fibrillation in the guinea pig heart." *J Cardiovasc Electrophysiol* 14(6): 621-31.

Wijffels, M. C., C. J. Kirchhof, et al. (1995). "Atrial fibrillation begets atrial fibrillation: a study in awake chronically instrumented goats." *Circulation* 92: 1954-1968.

The invention claimed is:

1. A method of analyzing a source of a complex rhythm disorder in a heart of a human, the method comprising:

accessing signals from a plurality of sensors disposed spatially in relation to the heart, the signals associated with activations of the heart, the signals being one or more of electrical, acoustic, electromagnetic, magnetic, microwave, and combinations thereof;

identifying a region of the heart including an activation trail that is rotational or radially emanating, the activation trail indicative of the source of the complex rhythm disorder, wherein the activation trail is based on the activations of the heart; and generating a clinical representation of the activation trail of activations that identifies the region of the heart associated with the indicated source.

2. The method of claim 1, wherein the signals are stored in a computer-accessible memory.

3. The method of claim 1, wherein the complex rhythm disorder comprises one of atrial fibrillation, ventricular fibrillation, and ventricular tachycardia.

4. The method of claim 1, wherein the complex rhythm disorder is atrial fibrillation and the activation trail is indicative of the atrial fibrillation.

5. The method of claim 1, wherein the activation trail comprises a rotor.

6. The method of claim 1, wherein identifying the region of the heart comprises arranging the activations of the signals to identify the activation trail of the region.

7. The method of claim 6, wherein the activations are arranged in a sequence based on one or more of timing of the activations, timing related to shapes of the signals, spatial relationship of sensors related to the signals, and phase of the signals.

8. The method of claim 1, wherein the method further comprises identifying a core region around which the activation trail rotates or from which the activation trail radially emanates, wherein the region comprises the core region.

9. The method of claim 8, wherein the method further comprises selecting a portion of the core region to facilitate modification of the portion of the core region for elimination of the activation trail.

10. The method of claim 1, wherein the activation trail is repeating.

11. The method of claim 1, wherein the complex rhythm disorder comprises atrial fibrillation.

12. A method of analyzing a source of a complex rhythm disorder in a heart of a human, the method comprising:
    accessing signals from a plurality of sensors disposed spatially in relation to the heart, the signals associated with activations of the heart;
    identifying a region of the heart including an activation trail, the activation trail based on a direct phase method, the activation trail comprising activations of the heart that revolve around or radially emanate from a core region, wherein the region comprises the core region that is interior to the activation trail, and wherein the core region is indicative of the source of the complex rhythm disorder; and
    generating a clinical representation of the activation trail of activations that identifies the region of the heart associated with the indicated source.

13. The method of claim 12, wherein the method further comprises selecting a portion of the region based at least on the activation trail to facilitate modification of the portion of the region for elimination of the activation trail.

14. The method of claim 12, wherein the method further comprises selecting a portion of the region adjacent the activation trail to facilitate modification of the portion of the region for isolation or migration of the activation trail.

15. The method of claim 12, wherein the method further comprises selecting a portion of the core region to facilitate modification of the portion of the core region for elimination of the activation trail.

16. The method of claim 12, wherein the activation trail comprises a rotor.

17. The method of claim 12, wherein the signals are stored in a computer-accessible memory.

18. The method of claim 12, wherein identifying the region of the heart comprises arranging the activations associated with the signals to identify the activation trail of the region.

19. The method of claim 12, wherein the activations are arranged in a sequence based on one or more of: timing of the activations, timing related to shapes of the signals, spatial relationship of sensors related to the signals, and phase of the signals.

20. The method of claim 12, wherein the method further comprises identifying a core region around which the activation trail revolves or from which the activation trail radially emanates.

21. The method of claim 20, wherein the method further comprises selecting a portion of the core region to facilitate modification of the portion of the core region for elimination of the activation trail.

22. The method of claim 12, wherein the activation trail is repeating.

23. A method of analyzing a source of a complex rhythm disorder in a heart of a human, the method comprising:
    accessing signals from a plurality of sensors disposed spatially in relation to the heart, the signals associated with activations of the heart;
    identifying a region of the heart including an activation trail, the activation trail based on a Hilbert transform, the activation trail comprising activations of the heart that revolve around or radially emanate from a core region, wherein the region of the heart comprises the core region that is interior to the activation trail, and wherein the core region is indicative of the source of the complex rhythm disorder; and
    generating a clinical representation of the activation trail of activations that identifies the region of the heart associated with the indicated source.

24. The method of claim 23, wherein the method further comprises selecting a portion of the region based at least on the activation trail to facilitate modification of the portion of the region for elimination of the activation trail.

25. The method of claim 23, wherein the method further comprises selecting a portion of the region adjacent the activation trail to facilitate modification of the portion of the region for isolation or migration of the activation trail.

26. The method of claim 23, wherein the method further comprises selecting a portion of the core region to facilitate modification of at least the portion of the core region for elimination of the activation trail.

27. The method of claim 23, wherein the activation trail comprises a rotor.

28. The method of claim 23, wherein the signals are stored in a computer-accessible memory.

29. The method of claim 23, wherein the complex rhythm disorder comprises one of atrial fibrillation, ventricular fibrillation, and ventricular tachycardia.

30. The method of claim 23, wherein the complex rhythm disorder is atrial fibrillation and the activation trail is indicative of atrial fibrillation.

31. The method of claim 23, wherein identifying the region of the heart comprises arranging the activations associated with the signals to identify the activation trail of the region.

32. The method of claim 31, wherein the activations are arranged in a sequence based on one or more of: timing of the activations, timing related to shapes of the signals, spatial relationship of sensors related to the signals, and phase of the signals.

33. The method of claim 23, wherein the method further comprises identifying a core region around which the activation trail revolves or from which the activation trail radially emanates.

34. The method of claim 33, wherein the method further comprises selecting a portion of the core region to facilitate modification of the portion of the core region for elimination of the activation trail.

35. The method of claim 23, wherein the activation trail is repeating.

36. The method of claim 35, wherein the method further comprises generating a clinical representation of the activation trail.

37. A method of analyzing a source of a complex rhythm disorder in a heart of a human, the method comprising:
accessing signals from a plurality of sensors disposed spatially in relation to the heart, the signals associated with activations of the heart;
identifying a region of the heart including an activation trail, the activation trail based on a time-domain method, the activation trail comprising activations of the heart that revolve around or radially emanate from a core region, wherein the region of the heart comprises the core region that is interior to the activation trail, and wherein the core region is indicative of the source of the complex rhythm disorder; and
generating a clinical representation of the activation trail of activations that identifies the region of the heart associated with the indicated source.

38. The method of claim 37, wherein the method further comprises selecting a portion of the region based at least on the activation trail to facilitate modification of the portion of the region for elimination of the activation trail.

39. The method of claim 37, wherein the method further comprises selecting a portion of the region adjacent the activation trail to facilitate modification of the portion of the region for isolation or migration of the activation trail.

40. The method of claim 37, wherein the method further comprises selecting a portion of the core region to facilitate modification of at least the portion of the core region for elimination of the activation trail.

41. The method of claim 37, wherein the activation trail comprises a rotor.

42. The method of claim 37, wherein the signals are stored in a computer-accessible memory.

43. The method of claim 37, wherein the complex rhythm disorder comprises one of atrial fibrillation, ventricular fibrillation, and ventricular tachycardia.

44. The method of claim 37, wherein the complex rhythm disorder is atrial fibrillation and the activation trail is indicative of atrial fibrillation.

45. The method of claim 37, wherein identifying the region of the heart comprises arranging activations associated with the signals to identify the activation trail of the region.

46. The method of claim 45, wherein the activations are arranged in a sequence based on one or more of: timing of the activations, timing related to shapes of the signals, spatial relationship of sensors related to the signals, and phase of the signals.

47. The method of claim 37, wherein the method further comprises identifying a core region around which the activation trail revolves or from which the activation trail radially emanates.

48. The method of claim 47, wherein the method further comprises selecting a portion of the core region to facilitate modification of the portion of the core region for elimination of the activation trail.

49. The method of claim 37, wherein the activation trail is repeating.

50. The method of claim 49, wherein the method further comprises generating a clinical representation of the activation trail.

51. A method of analyzing a source of a complex rhythm disorder in a heart of a human, the method comprising:
accessing signals from a plurality of sensors disposed spatially in relation to the heart, the signals associated with activations of the heart;
identifying a region of the heart including an activation trail, the activation trail created using one of a direct phase method, Hilbert transform and time-domain method, the activation trail comprising activations of the heart that revolve around or radially emanate from a core region, the core region being interior to the activation trail, wherein the core region is indicative of the source of the complex rhythm disorder; and
generating a clinical representation of the activation trail of activations that identifies the region of the heart associated with the indicated source.

52. The method of claim 51, wherein the method further comprises selecting a portion of the region based at least on the activation trail to facilitate modification of the portion of the region for elimination of the activation trail.

53. The method of claim 51, wherein the method further comprises selecting a portion of the region adjacent the activation trail to facilitate modification of the portion of the region for isolation or migration of the activation trail.

54. The method of claim 51, wherein the method further comprises selecting a portion of the core region to facilitate modification of the portion of the core region for elimination of the activation trail.

55. The method of claim 51, wherein the activation trail comprises a rotor.

56. The method of claim 51, wherein the signals are stored in a computer-accessible memory.

57. The method of claim 51, wherein the complex rhythm disorder comprises one of atrial fibrillation, ventricular fibrillation, and ventricular tachycardia.

58. The method of claim 51, wherein the complex rhythm disorder is atrial fibrillation and the activation trail is indicative of atrial fibrillation.

59. The method of claim 51, wherein identifying the region of the heart comprises arranging activations associated with the signals to identify the activation trail of the region.

60. The method of claim 59, wherein the activations are arranged in a sequence based on one or more of: timing of the activations, timing related to shapes of the signals, spatial relationship of sensors related to the signals, and phase of the signals.

61. The method of claim 51, wherein the method further comprises identifying a core region around which the activation trail revolves or from which the activation trail radially emanates.

62. The method of claim 61, wherein the method further comprises selecting a portion of the core region to facilitate modification of the portion of the core region for elimination of the activation trail.

63. The method of claim 51, wherein the activation trail is repeating.

64. The method of claim 63, wherein the method further comprises generating a clinical representation of the activation trail.

65. The method of claim 51, wherein the complex rhythm disorder comprises atrial fibrillation.

66. A method of analyzing a source of a complex rhythm disorder in a heart of a human, the method comprising:

accessing information representative of activations of the heart while the heart experiences the complex rhythm disorder, the information being one or more of electrical, acoustic, electromagnetic, magnetic, microwave, and combinations thereof;

processing the information to identify a region of the heart including an activation pattern that is rotational or radially emanating, the activation pattern indicative of the source of the complex rhythm disorder, wherein the activation pattern is based on activations of the heart; and generating a clinical representation of the activation pattern of activations that identifies the region of the heart associated with the indicated source.

67. The method of claim 66, wherein the method further comprises selecting a portion of the region of the heart based at least on the activation pattern to facilitate modification of the portion of the region for elimination of the activation pattern.

68. The method of claim 66, wherein the activation pattern comprises a rotor.

69. The method of claim 66, wherein processing the information to identify the region of the heart comprises arranging the activations to identify the activation pattern of the region.

70. The method of claim 69, wherein the activations are arranged in a sequence based on one or more of: timing of the activations, timing related to shapes of the information, spatial relationship of sensors related to the information, and phase of the information.

71. The method of claim 66, wherein the method further comprises identifying a core region around which the activation pattern rotates or from which the activation pattern radially emanates.

72. The method of claim 71, wherein the method further comprises selecting a portion of the core region to facilitate modification of the portion of the core region for elimination of the activation pattern.

73. The method of claim 66, wherein the activation pattern is repeating.

74. A method of analyzing a source of a complex rhythm disorder in a heart of a human, the method comprising:

accessing information representative of activations of the heart while the heart experiences the complex rhythm disorder;

identifying a region of the heart having activations that revolve around or radially emanate from a core region, wherein the region of the heart comprises the core region that is interior to an activation trail, and wherein a pattern of the activations is based on at least one of a phase method, time domain method and Hilbert transform, wherein the pattern of the activations is indicative of the source of the complex rhythm disorder; and generating a clinical representation of the pattern of the activations that identifies the region of the heart associated with the indicated source.

75. The method of claim 74, wherein the pattern of the activations comprises a rotor.

76. The method of claim 74, wherein identifying the region of the heart comprises arranging activations associated with the activations to identify the pattern of the activations.

77. The method of claim 76, wherein the activations are arranged in a sequence based on one or more of: timing of the activations, timing related to shapes of the information, spatial relationship of sensors related to the information, and phase of the information.

78. The method of claim 74, wherein the method further comprises identifying a core region around which the pattern of activations rotates or from which the activation pattern radially emanates.

79. The method of claim 78, wherein the method further comprises selecting a portion of the core region to facilitate modification of the portion of the core region for elimination of the pattern of activations.

80. The method of claim 78, wherein the method further comprises selecting at least a portion of an area adjacent the core region to facilitate modification of at least the portion of the area adjacent the core region for isolation or migration of the activation pattern.

81. The method of claim 74, wherein the method further comprises generating a clinical representation of the pattern of activations.

* * * * *